United States Patent [19]
Shinoda et al.

[11] Patent Number: 5,743,857
[45] Date of Patent: Apr. 28, 1998

[54] BLOOD PRESSURE MONITOR APPARATUS

[75] Inventors: Masayuki Shinoda, Tajimi; Hidekatsu Inukai, Nagoya; Hiroshi Sakai, Komaki, all of Japan

[73] Assignee: Colin Corporation, Komaki, Japan

[21] Appl. No.: 704,576

[22] PCT Filed: Jan. 12, 1996

[86] PCT No.: PCT/JP96/00039

§ 371 Date: Sep. 10, 1996

§ 102(e) Date: Sep. 10, 1996

[87] PCT Pub. No.: WO96/22050

PCT Pub. Date: Jul. 25, 1996

[30] Foreign Application Priority Data

Jan. 17, 1995 [JP] Japan ................ 7-4806
Dec. 20, 1995 [JP] Japan ................ 7-332076

[51] Int. Cl.⁶ ............................................. A61B 5/00
[52] U.S. Cl. ........................ 600/496; 600/492; 600/494
[58] Field of Search .......................... 128/672, 679–683; 600/485, 492–496

[56] References Cited

U.S. PATENT DOCUMENTS

| | | | |
|---|---|---|---|
| 4,907,596 | 3/1990 | Schmid et al. | 128/672 |
| 5,261,414 | 11/1993 | Aung et al. | |
| 5,279,303 | 1/1994 | Kawamura et al. | 128/683 |
| 5,309,916 | 5/1994 | Hatschek | 128/672 |
| 5,564,427 | 10/1996 | Aso et al. | 128/681 |
| 5,606,977 | 3/1997 | Ramsey et al. | 128/681 |

FOREIGN PATENT DOCUMENTS

| | | |
|---|---|---|
| 3-15440 | 1/1991 | Japan . |
| 3-505533 | 12/1991 | Japan . |
| 4-200439 | 7/1992 | Japan . |
| 5-3858 | 1/1993 | Japan . |
| 5-146415 | 6/1993 | Japan . |
| 6-38933 | 2/1994 | Japan . |
| 6-319706 | 11/1994 | Japan . |
| 7-136136 | 5/1995 | Japan . |

*Primary Examiner*—William E. Kamm
*Assistant Examiner*—George R. Evanisko
*Attorney, Agent, or Firm*—Oliff & Berridge, PLC

[57] ABSTRACT

A blood pressure measurement of a blood pressure measuring device is terminated by a blood pressure measurement terminating device, when a difference $|D_M - D_{CP}|/D_{CP}$ between a phase difference $D_M$ obtained according to a phase difference-blood pressure relationship based on a monitor blood pressure value MBP determined by a monitor blood pressure determining device, and an actual phase difference $D_{CP}$ obtained by a phase difference calculating device, when the blood pressure measurement of the blood pressure measuring device starts, is smaller than a reference value $\alpha$. Thus, so long as the pressure pulse wave-blood pressure relationship is effectively applicable, no blood pressure measurement is carried out for updating the current pressure pulse wave-blood pressure relationship, so that the frequency of blood pressure measurements using a cuff is decreased and the discomfort of a living subject is reduced.

19 Claims, 14 Drawing Sheets

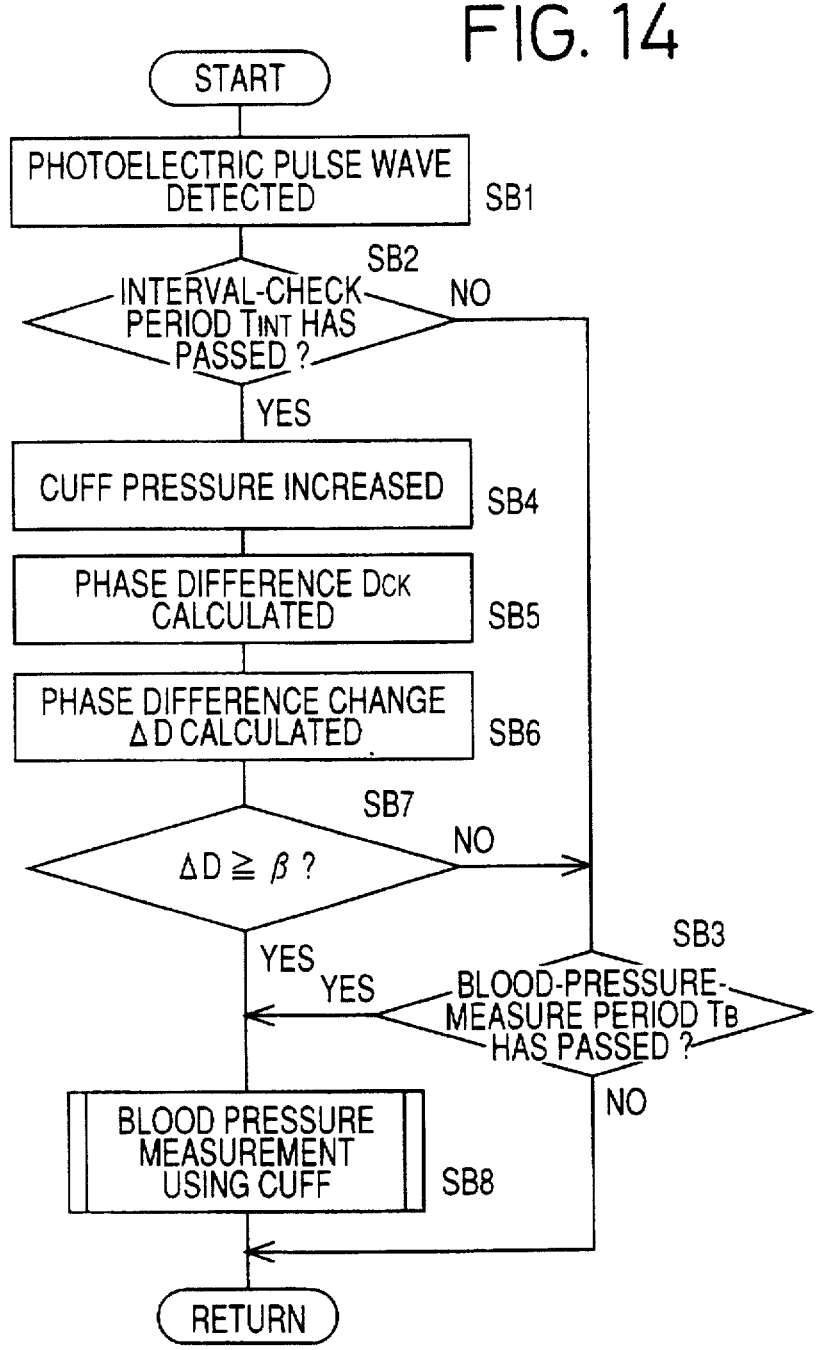

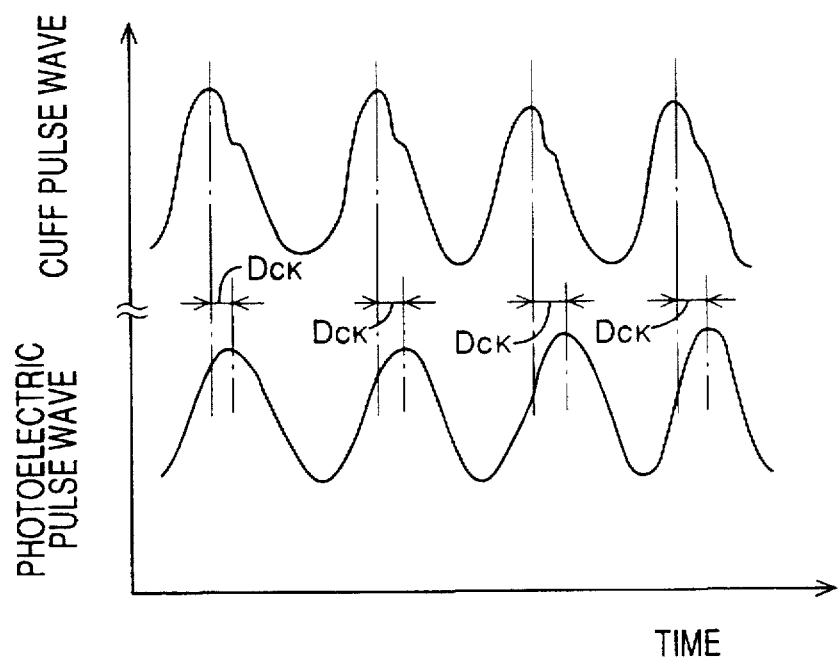

BLOOD PRESSURE MONITOR APPARATUS

FIELD OF THE ART

The present invention relates to a blood pressure monitor apparatus which monitors blood pressure values of a living subject for a considerably long time.

BACKGROUND OF THE INVENTION

Generally, a blood pressure monitor apparatus which monitors blood pressure values of a living subject for a considerably long time includes a cuff being worn on a portion of the subject and a blood pressure measuring device for measuring a blood pressure value of the subject by changing a pressure of the cuff. The blood pressure value measured by the blood pressure measuring device using the cuff enjoys high reliability. As one type of the above-mentioned blood pressure monitor apparatus, there is known an apparatus which starts a blood pressure measurement of a blood pressure measuring device and outputs the measured blood pressure values of a living subject at a predetermined period.

However, in the above blood pressure monitor apparatus, if the interval between successive blood pressure measurements is shortened for improving the accuracy of blood pressure monitoring, the frequency of pressing of the cuff is increased and the subject feels more discomfort. In the case where the frequency of pressing of the cuff is excessively high, congestion occurs to the body portion on which the cuff is worn, and accurate blood pressure values are not obtained.

Further, there has been proposed a monitor blood pressure apparatus including a blood pressure measuring device for measuring a blood pressure value of a living subject based on variation of a pulse-synchronous wave obtained by changing a pressure of a cuff being worn on the living subject, a pressure pulse wave sensor adapted to be pressed on an artery of the subject for detecting a pressure pulse wave produced from the artery of the subject, a pressure pulse wave-blood pressure relationship determining means for determining, at a predetermined period, a pressure pulse wave-blood pressure relationship between magnitude of pressure pulse wave and blood pressure based on the pressure pulse wave detected by the pulse wave sensor and the blood pressure measured by the blood pressure measuring device, by starting the blood pressure measuring device at the predetermined period, and a monitor blood pressure determining means for successively determining a monitor blood pressure value based on an actual pressure pulse wave detected by the pressure pulse wave sensor, according to the pressure pulse wave-blood pressure relationship. An example of the blood pressure monitor apparatus is disclosed in Laid-Open publication No. 5-3858 of Unexamined Japanese patent application. The blood pressure monitor apparatus is capable of detetermining a monitor blood pressure value for each heartbeat-synchronous pulse of a pulse wave.

However, since the blood pressure measurement using the cuff is carried out at the predetermined period to determine a pressure pulse wave-blood pressure relationship for maintaining the accuracy of monitor blood pressure values, the living subject feels discomfort due to the pressure of the cuff although the pressure pulse wave-blood pressure relationship may be effective.

The present invention has been developed in the background of the above-described situation. It is therefore an object of the present invention to provide a blood pressure monitor apparatus which monitors blood pressure values of a living subject, without having the subject feel discomfort.

The inventors of the present invention have found that there exists a phase difference between respective pulse waves detected by pulse wave sensors being worn on different portions of a living subject, and that the phase difference mainly depends on the distances between the heart of the subject and the pulse wave sensors. They have also found that the phase difference changes depending on the blood pressure of the subject. The present invention has been developed based on those findings. Thus, unnecessary blood pressure measurements using the cuff are avoided when it is judged, based on the phase difference, that the blood pressure of the living subject has not changed.

DISCLOSURE OF THE INVENTION

The above object may be achieved according to the first invention which provides a blood pressure monitor apparatus including a blood pressure measuring device for measuring a blood pressure value of a living subject based on variation of a pulse-synchronous wave obtained by changing a pressure of a cuff which is worn on the living subject, a pressure pulse wave sensor adapted to be pressed on an artery of the living subject for detecting a pressure pulse wave produced from the artery of the living subject, a pressure pulse wave-blood pressure relationship determining means for determining, at a predetermined period, a pressure pulse wave-blood pressure relationship between magnitude of pressure pulse wave and blood pressure, based on the pressure pulse wave detected by the pulse wave sensor and the blood pressure value measured by the blood pressure measuring device, by starting the blood pressure measuring device at the predetermined period, and a monitor blood pressure determining means for successively determining a monitor blood pressure value based on an actual pressure pulse wave detected by the pressure pulse wave sensor, according to the pressure pulse wave-blood pressure relationship, the blood pressure monitor apparatus comprising (a) a pair of heartbeat-synchronous wave sensors for detecting, on different portions of the living subject, respective heartbeat-synchronous waves produced in synchronism with a heartbeat of the living subject, (b) a phase difference calculating means for calculating a phase difference of the heartbeat-synchronous waves detected by the pair of heartbeat-synchronous wave sensors, (c) a phase difference-blood pressure relationship determining means for determining a phase difference-blood pressure relationship between phase difference and blood pressure, based on the phase difference calculated by the phase difference calculating means and the blood pressure value measured by the blood pressure measuring device, and (d) a blood pressure measurement terminating means for terminating a blood pressure measurement of the blood pressure measuring device, when a difference between a phase difference obtained according to the phase difference-blood pressure relationship based on a monitor blood pressure value determined by the monitor blood pressure determining means, and a phase difference obtained by the phase difference calculating means, when the blood pressure measurement of the blood pressure measuring device starts, is smaller than a reference value.

In the above-mentioned apparatus, when a phase difference of the respective pulse waves detected by the pair of heartbeat-synchronous wave sensors is calculated by the phase difference calculating means, a phase difference-blood pressure relationship is determined by the phase difference-blood pressure relationship determining means based on the phase difference calculated by the phase difference calculating means and the blood pressure measured by the blood pressure measuring device. Then, by the blood pressure measurement terminating means, a blood pressure measurement of the blood pressure measuring device is terminated, when a difference between a phase difference obtained according to the phase difference-blood pressure relationship based on a monitor blood pressure value determined by the monitor blood pressure determining means, and the phase difference obtained by the phase difference calculating means, when the blood pressure measurement of the blood pressure measuring device starts, is smaller than a reference value. Thus, when the pressure pulse wave-blood pressure relationship is effectively applicable, a blood pressure measurement for updating the pressure pulse wave-blood pressure relationship is not carried out, so that frequency of blood pressure measurements using the cuff is decreased and the discomfort of the living subject is reduced.

The pair of heartbeat-synchronous wave sensors may respectively be worn on different portions of the living subject, for example, left and right arms, upper arm and head, or arm and leg. When the pair of heartbeat-synchronous wave sensors are worn on the same portion of the living subject, it may be difficult to monitor the blood pressure of the subject with accuracy because the phase difference between the two pulse waves is small. The phase difference may be calculated by the phase difference calculating means from, for example, the interval between respective upper or lower peaks of two pulse waves which are detected by the pair of heartbeat-synchronous wave sensors substantially at the same time, or the interval between a predetermined point on an electrocardiographic waveform and a predetermined point on a pulse wave.

In the above-mentioned apparatus, one of the pair of heartbeat-synchronous wave sensors may comprise the cuff, a pressure sensor for detecting a pressure of the cuff, and a band-pass filter for extracting, as a cuff pulse wave, an oscillatory pressure wave produced in synchronism with the heartbeat of the living subject, from the pressure of the cuff detected by the pressure sensor, each of which is used as a part of the blood pressure measuring device. Thus, one of the pair of heartbeat-synchronous wave sensors may be shared by the blood pressure monitor device.

Further, the phase difference calculating means may be adapted to calculate the phase difference from the pulse wave detected from the cuff, when the increasing of the pressure of the cuff is started by the blood pressure measuring device.

Moreover, the other of the pair of heartbeat-synchronous wave sensors may comprise the pressure pulse wave sensor. Thus, the pressure pulse wave sensor may function as the other of the pair of heartbeat-synchronous wave sensors.

One of the pair of heartbeat-synchronous wave sensors may comprise an electrocardiographic waveform detecting device for detecting an electrocardiographic waveform through electrodes which are put on a surface of the living subject. For example, since an R wave of the electrocardiographic waveform corresponds to a lower-peak point of an aortic pressure waveform, the time difference between the R wave of the electrocardiographic waveform and the cuff pulse wave or the pressure pulse wave may be used as the phase difference.

The above object may be achieved according to another invention, which provides a blood pressure monitor apparatus including a blood pressure measuring device for measuring a blood pressure value of a living subject based on variation of a pulse-synchronous wave obtained by changing a pressure of a cuff which is worn on the living subject, a pressure pulse wave sensor adapted to be pressed on an artery of the living subject for detecting a pressure pulse wave produced from the artery of the living subject, a pressure pulse wave-blood pressure relationship determining means for determining, at a predetermined period, a pressure pulse wave-blood pressure relationship between magnitude of pressure pulse wave and blood pressure, based on the pressure pulse wave detected by the pulse wave sensor and the blood pressure measured by the blood pressure measuring device, by starting the blood pressure measuring device at the predetermined period, and a monitor blood pressure determining means for successively determining a monitor blood pressure value based on an actual pressure pulse wave detected by the pressure pulse wave sensor, according to the pressure pulse wave-blood pressure relationship, the blood pressure monitor apparatus comprising (a) an electrocardiographic waveform detecting device for detecting an electrocardiographic waveform of the living subject, (b) a phase difference calculating means for calculating a phase difference between the pressure pulse wave detected by the pressure pulse wave sensor and the electrocardiographic waveform detected by the electrocardiographic waveform detecting device, and (c) a starting means for starting a blood pressure measurement of the blood pressure measuring device, for updating the pressure pulse wave-blood pressure relationship, when a change of the monitor blood pressure values determined by the monitor blood pressure determining means differs from a change of respective inverses of the phase differences calculated by the phase difference calculating means.

In the above-mentioned apparatus, an electrocardiographic waveform of a living subject is detected by the electrocardiographic waveform detecting device, and a pressure pulse wave produced from an artery of the subject is detected by the pressure pulse wave sensor, so that a phase difference between the electrocardiographic waveform and the pressure pulse wave is calculated by the phase difference calculating means. Then, a monitor blood pressure value is determined by the monitor blood pressure determining means, based on the pressure pulse wave. Furthermore, a blood pressure measurement using the cuff by the blood pressure measuring device is started by the starting means, for updating the pressure pulse wave-blood pressure relationship, when the change of the monitor blood pressure values, for example, systolic blood pressure values, differs from the change of respective inverses of the phase differences. It is experimentally known that the change of respective inverses of the phase differences between the electrocardiographic waveform and the pressure pulse wave is proportional to the change of the monitor blood pressure values. Thus, only when the change of the monitor blood pressure values differs from the change of respective inverses of the phase differences, that is, the reliability of the monitor blood pressure values is doubtful, a blood pressure measurement using the cuff is started. Accordingly, it is possible to select a considerably long period at which each blood pressure measurements using the cuff is carried out for updating the pressure pulse wave-blood pressure relationship. Consequently the frequency of blood pressure measurements using the cuff is decreased and the discomfort of the living subject is reduced. In addition, the duration of continuation of each blood pressure monitoring operation is maximized.

The above-mentioned object may also be achieved by another invention, which provides a blood pressure monitor apparatus including a blood pressure measuring device for measuring, at a predetermined period, a blood pressure value of a living subject based on variation of a pulse wave obtained by changing a pressure of a cuff which is worn on the living subject, the blood pressure monitor apparatus comprising (a) a pair of heartbeat-synchronous wave sensors for detecting, on different portions of the living subject, respective heartbeat-synchronous waves produced in synchronism with a heartbeat of the living subject, (b) a phase difference calculating means for calculating a phase difference of the heartbeat-synchronous waves detected by the pair of heartbeat-synchronous wave sensors, (c) a phase difference change calculating means for calculating a change of the phase differences calculated by the phase difference calculating means, and (d) a starting means for starting a blood pressure measurement of the blood pressure measuring device, when the change of the phase differences calculated by the phase difference change calculating means is greater than a reference value.

In the above-mentioned apparatus, a phase difference of the heartbeat-synchronous waves detected by the pair of heartbeat-synchronous wave sensors is calculated by the phase difference calculating means, and then a change of the phase differences, for example, amount of change or ratio of change, is calculated by the phase difference change calculating means. By the starting means, a blood pressure measurement of the blood pressure measuring device is started, when a change of the phase differences is greater than a reference value. Thus, when the change of the phase differences is smaller than the reference value, that is, the change in the blood pressure values of the living subject is small and stable, no blood pressure measurement using the cuff is carried out, so that the frequency of blood pressure measurements is decreased and the discomfort of the subject is reduced.

The pair of heartbeat-synchronous wave sensors are respectively worn on different portions of the living subject, preferably, left and right arms, upper arm and head, or arm and leg. When the sensors are worn on the same portion of the subject, it is difficult to monitor the blood pressure because the phase difference between the pulse waves becomes small. The phase difference calculated by the phase difference calculating means may be the difference between respective upper or lower peaks of heartbeat-synchronous waves detected by the pair of heartbeat-synchronous wave sensors, for example, the difference between a predetermined point of a cuff pulse wave and a predetermined point of a pressure pulse wave, or the difference between a predetermined point of an electrocardiographic waveform and a predetermined point of a pulse wave.

Furthermore, the change of phase differences calculated by the phase difference change calculating means may be the rate or amount of change of a current phase difference from a prior phase difference at the beginning of each blood pressure monitoring operation, or a current moving average of phase differences.

In the above-mentioned apparatus, when the change of the phase differences is greater than the reference value, the starting means may start a blood pressure measurement of the blood pressure measuring device. So long as the change of the phase differences is not greater than the reference value, the starting means may not start a blood pressure measurement of the blood pressure measuring device.

Furthermore, one of the pair of heartbeat-synchronous wave sensors may include the cuff, a pressure sensor for detecting a pressure of the cuff, and a band-pass filter for extracting, as a cuff pulse wave, an oscillatory pressure wave produced in synchronism with the heartbeat of the living subject, from the pressure of the cuff detected by the pressure sensor. In this case, the cuff, pressure sensor, and band-pass filter employed as parts of the blood pressure measuring device are shared by one of the pair of heartbeat-synchronous wave sensors.

Moreover, the blood pressure monitor apparatus may further include a cuff-pressure increasing device which increases, at a predetermined period, the pressure of the cuff up to a predetermined value, for example, not higher than a mean blood pressure of the subject, preferably, not higher than a diastolic blood pressure of the subject, while the blood pressure measurements are not carried out by the blood pressure measuring device. In this case, the phase difference calculating means calculates a phase difference between a cuff pulse wave produced in the cuff inflated by the cuff-pressure increasing device and a heartbeat-synchronous wave detected by the other of the pair of heartbeat-synchronous wave sensors which is worn on a portion of the living subject different from a portion on which the cuff is worn. Thus, since the cuff pulse wave is detected by increasing, at a predetermined period, the pressure of the cuff up to the predetermined value, for example, not higher than a mean blood pressure, preferably, not higher than a diastolic blood pressure, the pressure of the cuff is kept low in detecting the cuff pulse wave and accordingly the subject is free from the discomfort.

Moreover, the other of the pair of heartbeat-synchronous wave sensors may include a photoelectric pulse wave sensor which emits light toward a body surface of the subject and detects a photoelectric pulse wave or a volumetric pulse wave, based on variation in quantity of light transmitted through, or reflected from, a portion of the living subject. Since this photoelectric pulse wave sensor may be employed as a probe of a pulse oximeter or a pulse-rate meter, the probe of the pulse oximeter or the pulse-rate meter may be used as the other of the pair of heartbeat-synchronous wave sensors, in the case where a continuous blood pressure measuring device carries out a blood pressure measurement at a predetermined period, and a pulse oximeter or a pulse-rate meter are used on the same living subject.

One of the pair of heartbeat-synchronous wave sensors may include an electrocardiographic waveform detecting device which detects an electrocardiographic waveform through electrodes put on a body surface of the living subject. For example, since an R wave of the electrocardiographic waveform corresponds to a lower peak of an aortic pressure waveform, the time difference between the R wave of the electrocardiographic waveform and the cuff pulse wave or pressure pulse wave may be used as the phase difference.

BRIEF DESCRIPTION OF THE DRAWINGS

FIG. 14 is a flow chart representing the operation of the control device of the apparatus of FIG. 11.

FIG. 15 is a view for illustrating a photoelectric pulse wave detected by a photoelectric pulse wave sensor of the apparatus of FIG. 11, and a cuff pulse wave detected by a pulse-wave filter circuit of the apparatus of FIG. 11.

THE BEST MODE FOR CARRYING OUT THE INVENTION

Figure 1:
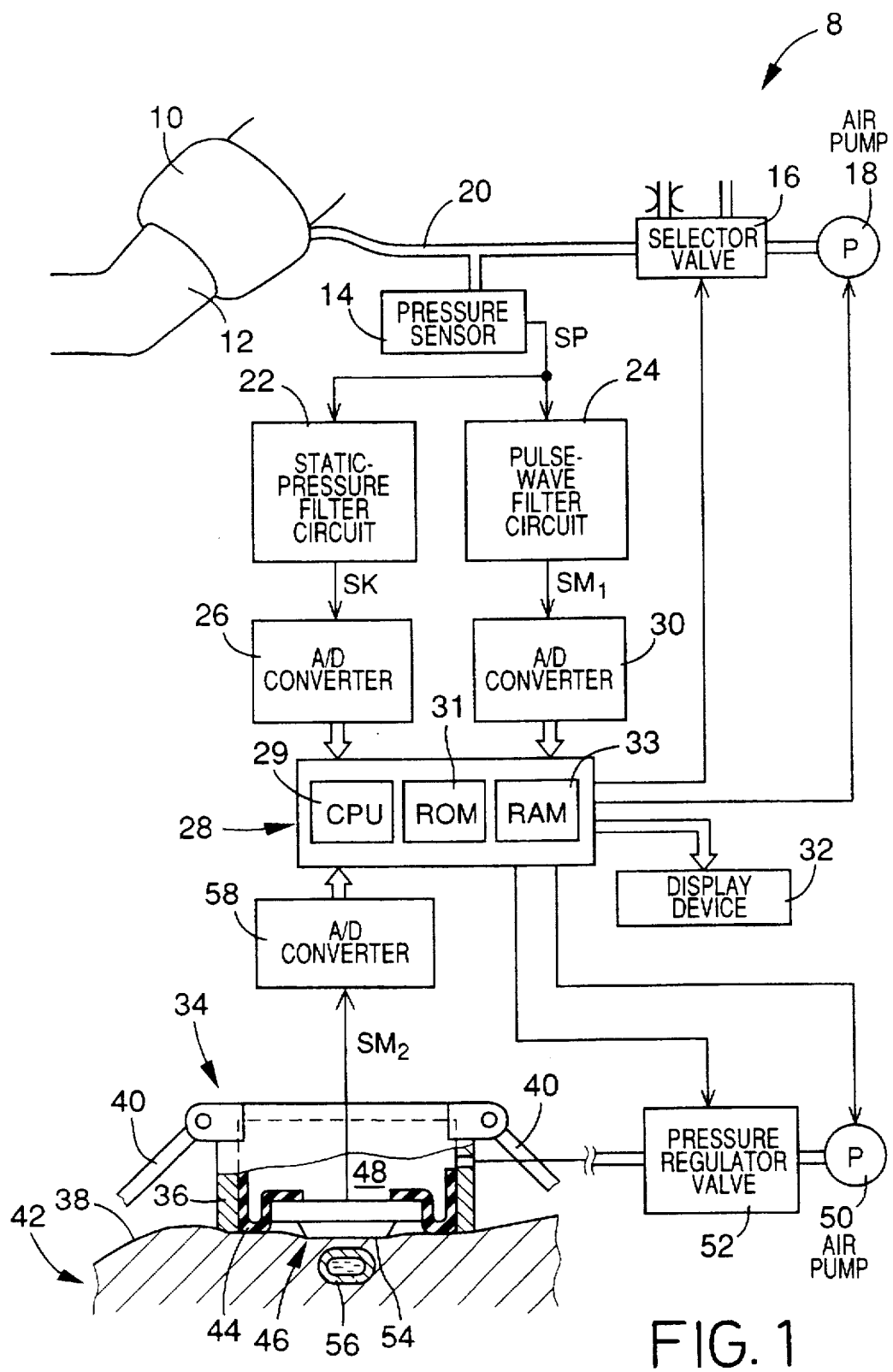
FIG. 1 is a diagrammatic view for illustrating the construction of a blood pressure monitor apparatus embodying the present invention.

There will be described in detail an embodiment of the present invention, referring to the drawings. FIG. 1 is a diagrammatic view for illustrating the construction of a blood pressure monitor apparatus 8 to which the above-indicated first invention is applied.

In FIG. 1, the blood pressure monitor apparatus 8 includes a cuff 10 which has a belt-like cloth bag and a rubber bag accommodated in the cloth bag and which is adapted to be wound around, e.g., an upper arm 12 of a patient, and a pressure sensor 14, a selector valve 16, and an air pump 18 each of which is connected to the cuff 10 via a piping 20. The selector valve 16 is selectively placed in an inflation position in which the selector valve 16 permits a pressurized air to be supplied to the cuff 10, a slow-deflation position in which the selector valve 16 permits the pressurized air to be slowly discharged from the cuff 10, and a quick-deflation position in which the selector valve 16 permits the pressurized air to be quickly discharged from the cuff 10.

The pressure sensor 14 detects an air pressure in the cuff 10, and supplies a pressure signal SP representative of the detected pressure to each of a static-pressure filter circuit 22 and a pulse-wave filter circuit 24. The static-pressure filter circuit 22 includes a low-pass filter and extracts, from the pressure signal SP, a static component contained in the signal SP, i.e., cuff pressure signal SK representative of the static cuff pressure. The cuff pressure signal SK is supplied to an electronic control device 28 via an A/D converter 26.

Figure 2:
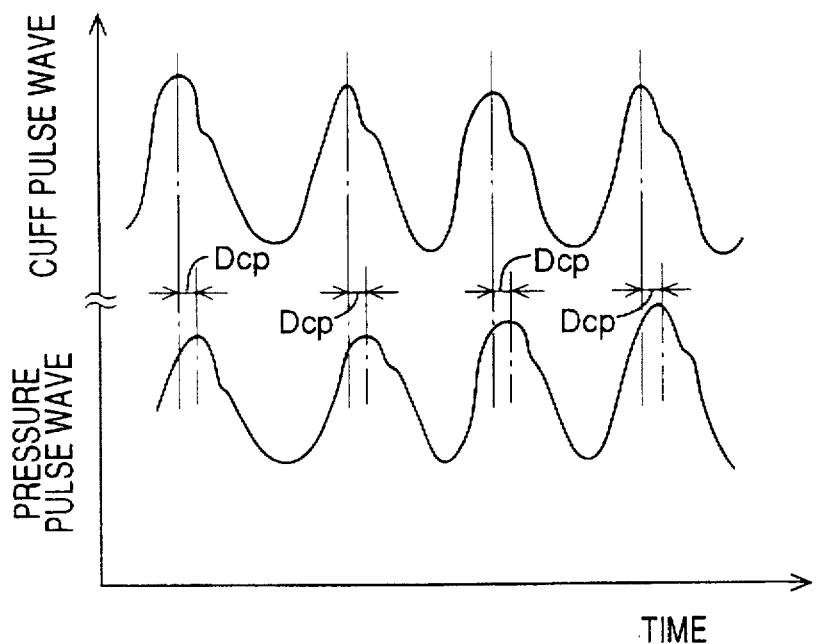
FIG. 2 is a view for illustrating a pressure pulse wave detected by a pressure pulse wave sensor of the apparatus of FIG. 1, and a cuff pulse wave detected by a pulse-wave filter circuit of the apparatus of FIG. 1.

The pulse-wave filter circuit 24 includes a band-pass filter and extracts, from the pressure signal SP, an oscillating component having predetermined frequencies, i.e., pulse wave signal $SM_1$. The pulse wave signal $SM_1$ is supplied to the electronic control device 28 via an A/D converter 30. The pulse wave signal $SM_1$ represents a cuff pulse wave, i.e., oscillatory pressure wave which is produced from a brachial artery (not shown) of the patient in synchronism with the heartbeat of the patient and is propagated to the cuff 10. In this embodiment, the cuff 10, the pressure sensor 14, and the pulse-wave filter circuit 24 cooperate with one another to function as one of a pair of heartbeat-synchronous wave sensors which detects the cuff pulse wave as a sort of heartbeat-synchronous wave. A waveform shown in an upper portion of FIG. 2 illustrates an example of the cuff pulse wave detected through the cuff 10.

The electronic control device 28 is provided by a so-called microcomputer including a CPU 29, a ROM 31, a RAM 33, and an I/O port (not shown). The CPU 29 processes signals according to control programs pre-stored in the ROM 31 by utilizing a temporary-storage function of the RAM 33, and supplies drive signals to the selector valve 16 and the air pump 18 through the I/O port.

The blood pressure monitor apparatus 8 further includes a pulse-wave detecting probe 34. The detecting probe 34 has a container-like housing 36 which is detachably set with the help of bands 40 on a body surface 38 of a wrist 42 of the patient, that is, body portion downstream of the upper arm 12 on which the cuff 10 is worn, such that an opening of the housing 36 is opposed to the body surface 38. A pressure pulse wave sensor 46 is supported by the housing 36 via a diaphragm 44, such that the pressure pulse wave sensor 46 is movable relative to the housing 36 and advanceable out of the opening of the housing 36. The housing 36, the diaphragm 44, etc. cooperate with one another to define a pressure chamber 48, to which a pressurized air is supplied from an air pump 50 via a pressure regulator valve 52. Thus, the pressure pulse wave sensor 46 is pressed against the body surface 38 with a pressing force $P_{HD}$ corresponding to the air pressure in the pressure chamber 48.

The pressure pulse wave sensor 46 includes a number of semiconductor pressure sensing elements (not shown) which are arranged in a pressing surface 54 of a semiconductor chip formed of, e.g., monocrystalline silicon. The pressure pulse wave sensor 46 is pressed on a radial artery 56 of the body surface 38 of the wrist 42 to detect, as a pressure pulse wave, an oscillatory pressure wave which is produced from the radial artery 56 and transmitted to the body surface 38, and generates a pulse wave signal $SM_2$ representative of the detected pressure pulse wave. The pulse wave signal $SM_2$ is supplied to the control device 28 via an A/D convertor 58. In the present embodiment, the pressure pulse wave sensor 46 functions as the other of the pair of heartbeat-synchronous wave sensors which detects the pressure pulse wave as a sort of heartbeat-synchronous wave. A waveform shown in a lower portion of FIG. 2 illustrates an example of the pressure pulse wave detected by the pressure pulse wave sensor 46.

The CPU 29 of the control device 28 operates, according to the control programs pre-stored in the ROM 31, for supplying drive signals to the air pump 50 and the pressure regulator valve 52, and thereby regulating an air pressure in the pressure chamber 48, that is, pressing force $P_{HD}$ of the pressure pulse wave sensor 46 against the body surface 38. Based on the pressure pulse waves successively obtained while the air pressure in the pressure chamber 48 is changed, the CPU 29 determines an optimum pressing force $P_{HDP}$ of the pressure pulse wave sensor 46, and controls the pressure regulator valve 52 to maintain the optimum pressing pressure $P_{HDP}$, for a blood pressure monitoring operation.

Figure 3:
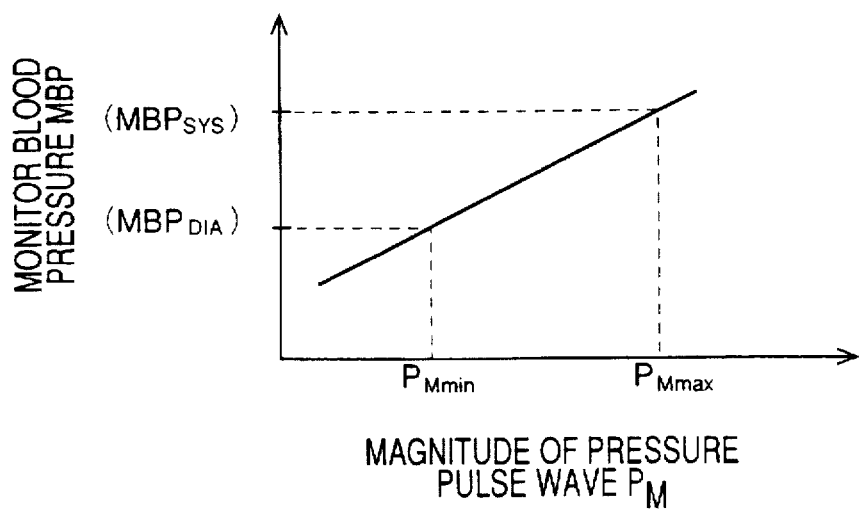
FIG. 3 is a graph showing a relationship used in the apparatus of FIG. 1.
Figure 4:
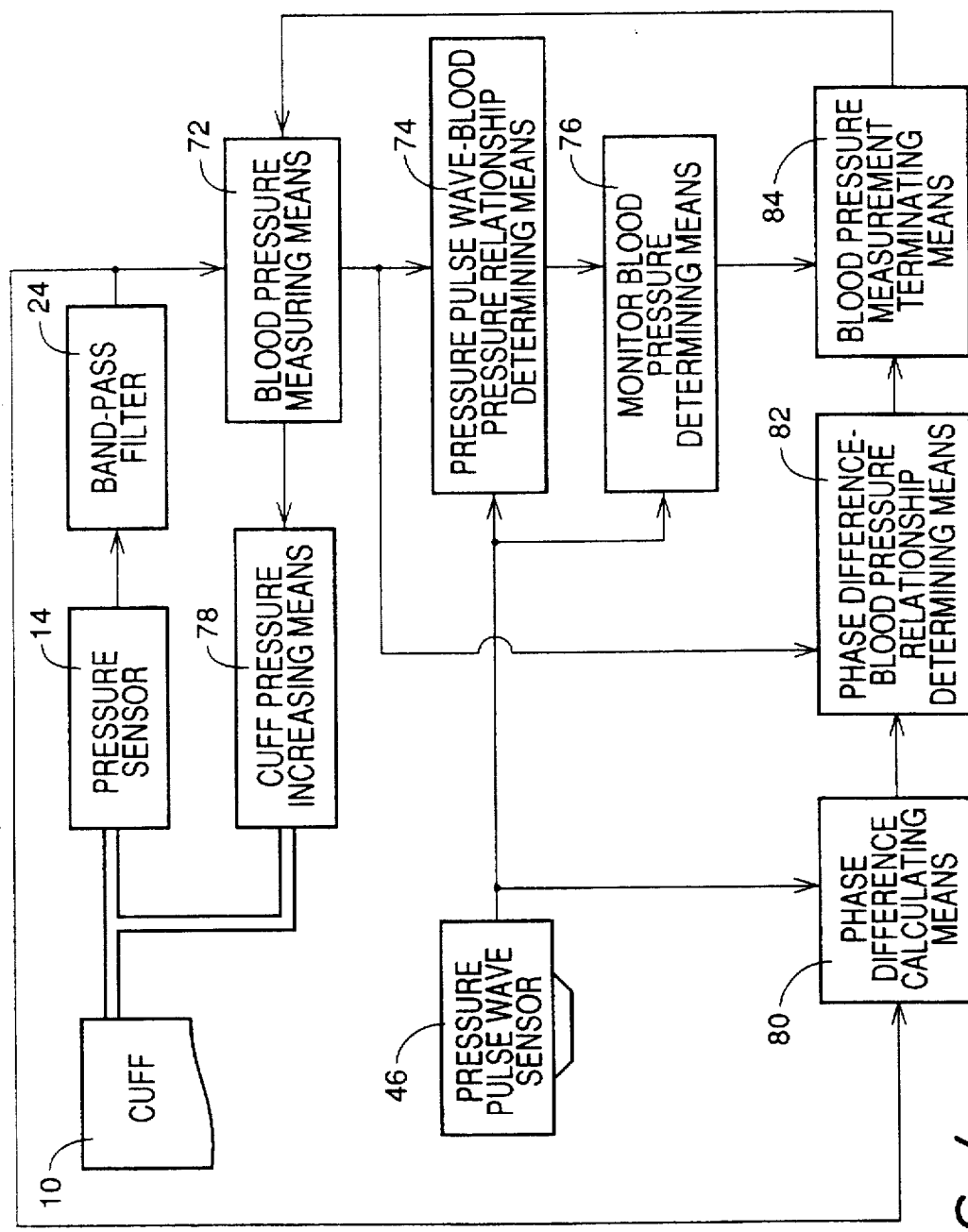
FIG. 4 is a block diagram for explaining various functions of a control device of the apparatus of FIG. 1.

FIG. 4 is a block diagram for explaining essential functions of the control device 28 of the blood pressure monitor apparatus 8. In the figure, a blood pressure measuring means 72 measures a systolic and a diastolic blood pressure value $BP_{SYS}$, $BP_{DIA}$, of the patient, according to an oscillometric method, based on the variation of respective magnitudes of pulses of the cuff pressure wave obtained as the pressure oscillation produced in the cuff 10 while the pressure of the cuff 10 is slowly changed. The pressure pulse wave sensor 46 is pressed on a body portion of the patient, such as the wrist 42, which is downstream of the body portion on which the cuff 10 is worn, such as the upper arm 12, and detects a pressure pulse wave produced from the radial artery 56 of the wrist 42. A pressure pulse wave-blood pressure relationship determining means 74 determines, in advance, a relationship between magnitude $P_M$ of pressure pulse wave and blood pressure value (monitor blood pressure value MBP), based on the pressure pulse wave detected by the pressure pulse wave sensor 46 and the blood pressure measured by the blood pressure measuring means 72, for an individual patient. This relationship may be one shown in FIG. 3 and be defined by the following expression: MBP= $A \cdot P_M + B$, where A is a constant indicative of the slope and B is a constant indicative of the intersept. A monitor blood pressure determining means 76 successively determines, according to the relationship, a systolic and a diastolic blood pressure value $MBP_{SYS}$, $MBP_{DIA}$ (monitor blood pressure values), based on magnitudes $P_M$ of each pulse of the pressure pulse wave detected by the pressure pulse wave sensor 46, that is, maximum (upper-peak) and minimum (lower-peak) magnitudes $P_{M2max}$, $P_{M2min}$ of each pulse of the pressure pulse wave, and successively outputs the detected monitor blood pressure values to a display device 32. A cuff-pressure increasing means 78 changes the pressing pressure of the cuff 10 in a well known procedure during each blood pressure measuring operation of the blood pressure measuring means 72 that is started at a predetermined period for updating the relationship. For example, the cuff pressure increasing means 78 increases the pressure of the cuff 10 up to a predetermined target value about 180 mmHg which is higher than a systolic blood pressure of the patient, and then slowly decreases it at about 3 mmHg/sec while the blood pressure measurement algorithm is carried out. Upon termination of the blood pressure measurement, the cuff-pressure increasing means 78 releases the pressure of the cuff 10.

Figure 5:
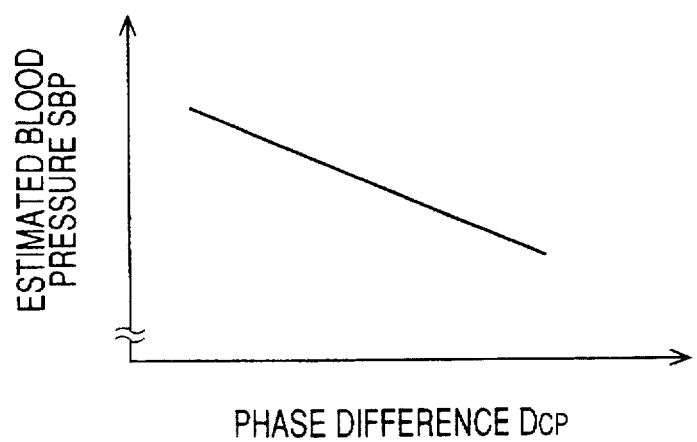
FIG. 5 is a graph showing a relationship between phase difference and estimated blood pressure that is used in the apparatus of FIG. 1.

Meanwhile, a phase difference calculating means 80 successively calculates a phase difference $D_{CP}$ between the pressure pulse wave detected by the pressure pulse wave sensor 46 and the cuff pulse wave obtained through the cuff 10 at an early stage of each blood pressure measurement of the blood pressure measuring device 72. A phase difference-blood pressure relationship determining means 82 determines a relationship between phase difference $D_{CP}$ and blood pressure, based on the phase difference values calculated by the phase difference calculating means 80 and the blood pressure values measured by the blood pressure measuring means 72. FIG. 5 shows the phase difference-blood pressure relationship. A blood pressure measurement terminating means 84 terminates a current blood pressure measurement of the blood pressure measuring means 72, when a difference, $|D_M - D_{CP}|$, between a phase difference $D_M$ obtained according to the phase difference-blood pressure relationship based on a monitor blood pressure value determined by the monitor blood pressure determining means 76, and a phase difference $D_{CP}$ obtained by the phase difference calculating means 80, when the blood pressure measurement of the blood pressure measuring means 72 starts, is smaller than a reference value α.

Figure 6:
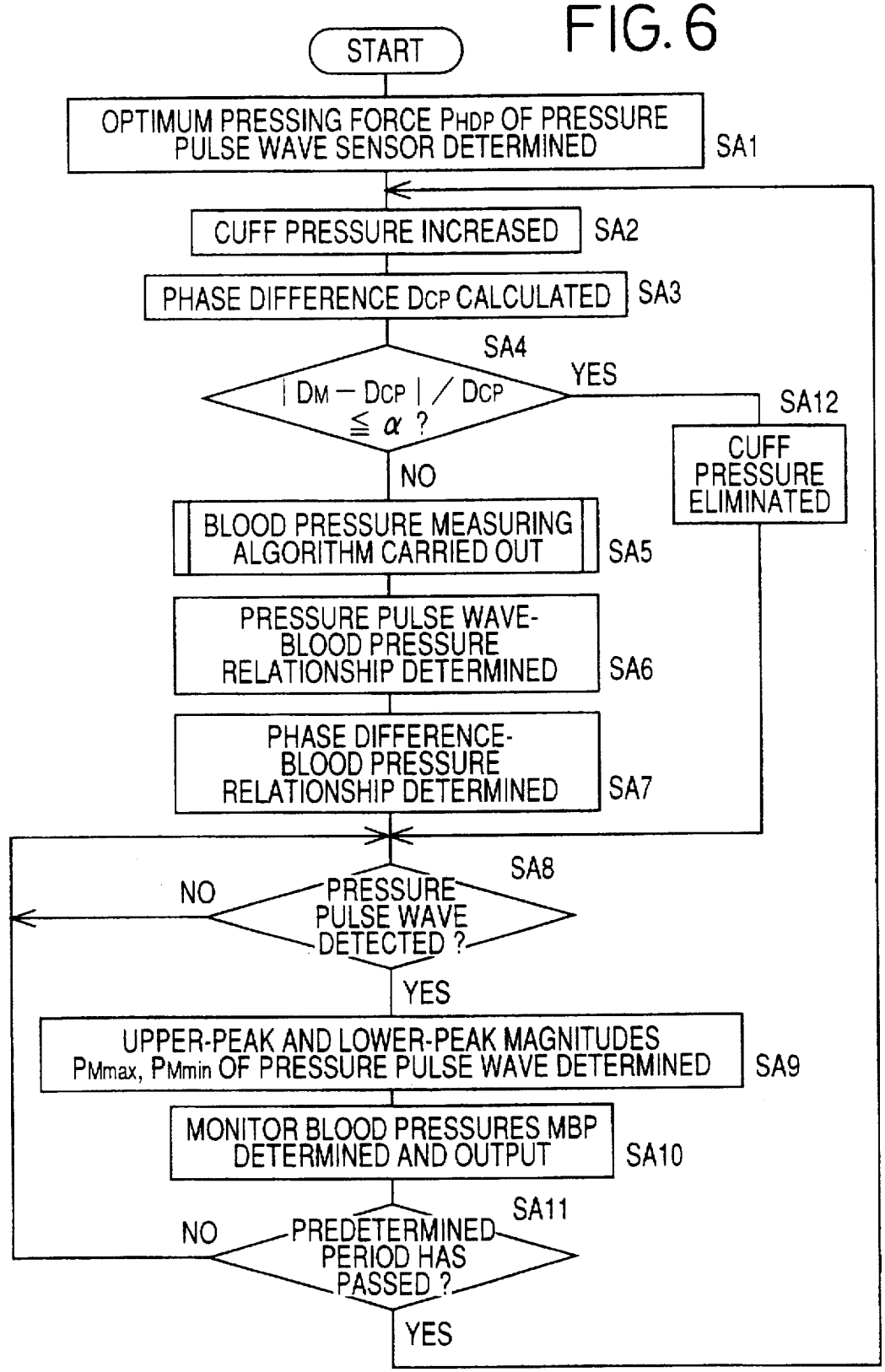
FIG. 6 is a flow chart representing the operation of the control device of the apparatus of FIG. 1.

FIG. 6 is a flow chart representing the operation of the control device 28. At Step SA1, the CPU 29 determines, as an optimum pressing force $P_{HDP}$ of the pressure pulse wave sensor 46, a pressure in the pressure chamber 48 when the respective amplitudes of pulses of the pressure pulse wave successively detected by the pressure pulse wave sensor 46 become maximum while the pressure of the pressure chamber 48 is slowly increased. With the pressure in the pressure chamber 48 being held at the optimum pressing force $P_{HDP}$, the pressure pulse wave sensor 46 is pressed on the body surface 38 with the constant, optimum pressing force $P_{HDP}$.

Step SA1 is followed by Step SA2, corresponding to the cuff-pressure increasing means 78, to start increasing the pressure of the cuff 10 for a blood pressure measurement. Step SA2 is followed by Step SA3, corresponding to the phase difference calculating means 80, to read in the pressure pulse wave detected by the pressure pulse wave sensor 46 and the cuff pulse wave detected through the cuff 10, and obtain the phase difference $D_{CP}$ by calculating a time difference between, e.g., an upper-peak point of a pulse of the pressure pulse wave and an upper-peak point of a corresponding pulse of the cuff pulse wave, as shown in FIG. 2.

Subsequently, the control of the CPU 29 goes to Step SA4, corresponding to the blood pressure measurement terminating means 84, to judge whether or not a difference $|D_M - D_{CP}|/D_{CP}$ between a phase difference $D_M$ obtained according to a phase difference-blood pressure relationship shown in FIG. 5, based on a monitor blood pressure value MBP, and the phase difference $D_{CP}$ obtained at Step SA3, when the increasing of the cuff pressure is started, i.e., when the current blood pressure measurement is started, is smaller than a reference value α. The reference value α is used as a criterion for judging whether or not the current pressure pulse wave-blood pressure relationship shown in FIG. 3 should be updated. For example, the reference value α is pre-determined to fall within from 5 to 10%.

Since at the early stage neither the phase difference-blood pressure relationship nor the monitor blood pressure value MBP have not been obtained, a negative judgment is made at Step SA4, so that the control of the CPU 29 proceeds with Step SA5, corresponding to the blood pressure measuring means 72, to carry out the blood pressure measuring algorithm. That is, the selector valve 16 is switched to the inflation position, and the air pump 18 is operated to increase, following the increasing of the cuff pressure at Step SA2, the cuff pressure up to a predetermined target value which is higher than an estimated systolic blood pressure of the patient (for example, 180 mmHg). Then, the air pump 18 is stopped and the selector valve 16 is switched to the slow-deflation position in which the selector valve 16 permits the pressurized air to be slowly discharged from the cuff 10. A systolic blood pressure value $BP_{SYS}$, a mean blood pressure value $BP_{MEAN}$, and a diastolic blood pressure value $BP_{DIA}$ are measured, according to the well known oscillometric type blood pressure determining algorithm, based on the variation of respective amplitudes of pulses of the cuff pulse wave represented by the pulse wave signal $SM_1$ obtained while the cuff pressure is slowly decreased at a predetermined low rate of about 3 mmHg/sec, and a pulse rate is determined based on the interval of successive two pulses of the cuff pulse wave. The thus measured blood pressure values and pulse rate are displayed by the display device 32, and the selector valve 16 is switched to the quick-deflation position in which the selector valve 16 permits the pressurized air to be quickly discharged from the cuff 10.

Next, Step SA5 is followed by Step SA6, corresponding to the pressure pulse wave-blood pressure relationship determining means 74, to obtain a relationship between magnitude $P_M$ of pressure pulse wave and blood pressure, shown in FIG. 3, based on the pressure pulse wave detected by the pressure pulse wave sensor 46 (absolute value, that is, magnitude of pulse wave signal $SM_2$) and the blood pressure values $BP_{SYS}$, $BP_{DIA}$ measured using the cuff 10 at Step SA5. More specifically described, one heartbeat-synchronous pulse of the pressure pulse wave detected by the pressure pulse wave sensor 46 is read in by the CPU 29, and an upper-peak magnitude $P_{M2max}$ and a lower-peak magnitude $P_{M2min}$ of the one pulse are determined by the CPU 29. Then, the relationship between magnitude of pressure pulse wave and blood pressure is determined, based on the upper-peak and lower-peak magnitudes $P_{M2max}$, $P_{M2min}$ of the pressure pulse wave and the systolic and diastolic blood pressure values $BP_{SYS}$, $BP_{DIA}$ measured at Step SA5.

Step SA6 is followed by Step SA7, corresponding to the phase difference-blood pressure relationship determining means 82, to determine a phase difference-blood pressure relationship shown in FIG. 5, based on the phase difference $D_{CP}$ calculated at Step SA3 and the above-mentioned systolic and diastolic blood pressure values $BP_{SYS}$, $BP_{DIA}$.

Step SA7 is followed by Step SA8 to judge whether or not one pulse of the pressure pulse wave has been detected. If the judgment at Step SA8 is negative, the control of the CPU 29 waits until a positive judgment is made. If the judgment at Step SA8 is positive, the control of the CPU 29 goes to Steps SA9 and SA10 corresponding to the monitor blood pressure determining means 76. At Step SA9, the CPU 29 determines a maximum magnitude $P_{M2max}$ (upper-peak magnitude) and a minimum magnitude $P_{M2min}$ (lower-peak magnitude) of the pulse of the pressure pulse wave detected by the pressure pulse wave sensor 46 pressed at the optimum pressing force $P_{HDP}$. Step SA9 is followed by Step SA10 to determine a systolic and a diastolic blood pressure value $MBP_{SYS}$, $MBP_{DIA}$ (monitor blood pressure values) based on the maximum and minimum magnitudes $P_{M2max}$, $P_{M2min}$ of the pressure pulse wave according to the pressure pulse wave-blood pressure relationship determined at Step SA6, and control the display device 32 to display the determined monitor blood pressure values together with a continuous waveform of the pressure pulse wave.

Step SA10 is followed by Step SA11 to judge whether or not a predetermined period of about 10 to 20 minutes, i.e., calibration period has passed after a blood pressure measurement using the cuff 10 is carried out at Step SA5. If the judgment at Step SA11 is negative, Steps SA8 to SA11 as the blood pressure monitoring routine are repeated, and systolic and diastolic blood pressure values $MBP_{SYS}$, $MBP_{DIA}$ are continuously determined and displayed based on each of heartbeat-synchronous pulses of the pressure pulse wave until a positive judgment is made at SA11. If the judgment at SA11 is positive, the control of the CPU 29 goes to back to Step SA2 to updates the pressure pulse wave-blood pressure relationship.

Thus, the pressure pulse wave-blood pressure relationship and the phase difference-blood pressure relationship are determined. Then, so long as the pressure pulse wave-blood pressure relationship is applicable, a difference $|D_M-D_{CP}|/D_{CP}$ between a phase difference $D_M$ obtained based on a monitor blood pressure value MBP according to the phase difference-blood pressure relationship shown in FIG. 5 and a phase difference $D_{CP}$ calculated at Step SA3, when the increasing of the pressure of the cuff 10 is started for a blood pressure measurement, is relatively small. In this case, a positive judgment is made at Step SA4. Consequently the control of the CPU 29 goes to Step SA12 to release the pressurized air of the cuff 10 and terminate the current blood pressure measurement which has just been started at Step SA2. Then, the control of the CPU 29 goes to Step SA8. However, if the pressure pulse wave-blood pressure relationship is no longer applicable, the judgment at Step SA4 is negative, so that the CPU 29 goes to Step SA5 and the following steps to update the relationships.

In the present embodiment, the phase difference $D_{CP}$ of the respective pulse waves detected by the pair of heartbeat-synchronous wave sensors is calculated at Step SA3 corresponding to the phase difference calculating means 80. At Step SA7 corresponding to the phase difference-blood pressure determining means 82, the phase difference-blood pressure relationship between phase difference $D_{CP}$ and blood pressure is determined as shown in FIG. 5. At Step SA4 corresponding to the blood pressure measurement terminating means 84, the current blood pressure measurement by the blood pressure measuring means 72 is terminated if the difference $|D_M-D_{CP}|/D_{CP}$ between a phase difference $D_M$ obtained according to the phase difference-blood pressure relationship based on a monitor blood pressure value MBP determined at Step SA10 corresponding to the monitor blood pressure determining means 76, and the phase difference $D_{CP}$ obtained by the phase difference calculating means 80, when the blood pressure measurement is started in Step SA5 corresponding to the blood pressure measuring means 72, is smaller than the reference value $\alpha$. Therefore, so long as the pressure pulse wave-blood pressure relationship is effectively applicable, no blood pressure measurement for updating the current pressure pulse wave-blood pressure relationship is carried out. Thus, since no unnecessary blood pressure measurements are not carried out, the frequency of blood pressure measurements using the cuff is reduced and the discomfort of the living subject is decreased.

In the present embodiment, the phase difference $D_{CP}$ is determined from the cuff pulse wave as the pressure oscillation produced in the cuff 10 being used for a blood pressure measurement and the pressure pulse wave detected by the pressure pulse wave sensor 46 being used for continuous blood pressure monitoring. Therefore, it is not needed to newly employ a pair of heartbeat-synchronous wave sensors for obtaining the phase difference $D_{CP}$.

Next, there will be described another embodiment according to the present invention. Hereinafter, the same parts as those of the prior embodiment will be denoted by the same reference numerals and the description thereof is omitted.

Figure 7:
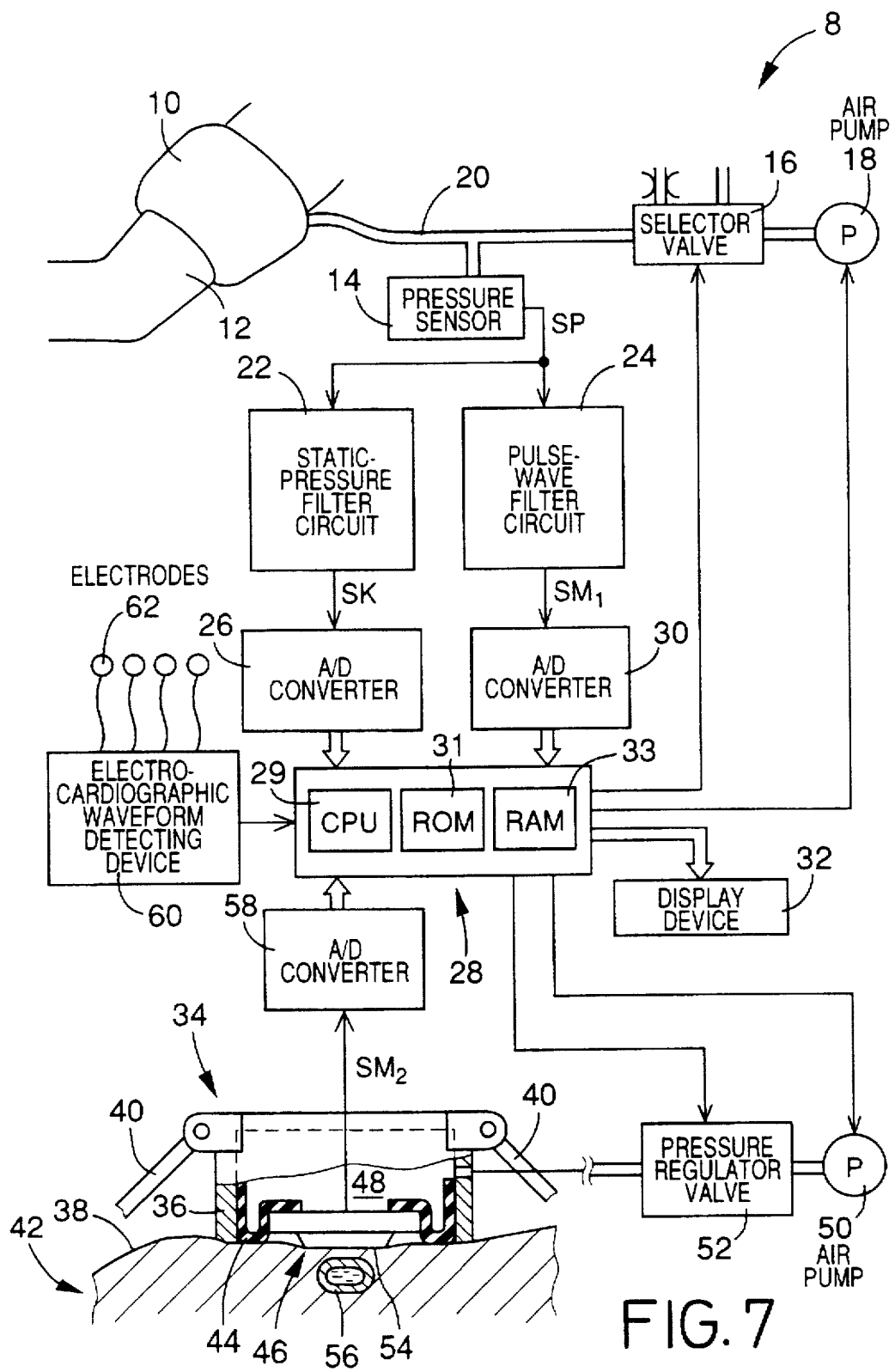
FIG. 7 is a diagrammatic view corresponding to FIG. 1, showing a blood pressure monitor apparatus as another embodiment according to the present invention.
Figure 8:
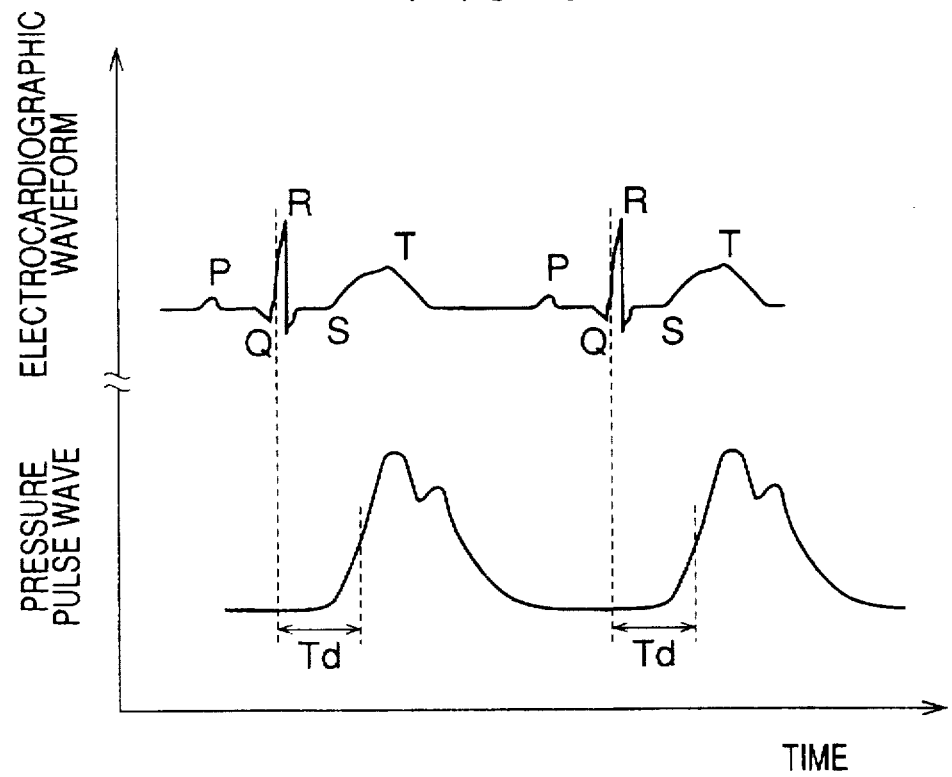
FIG. 8 is a view for illustrating a pressure pulse wave detected by a pressure pulse wave sensor 46 of the apparatus of FIG. 7, and an electrocardiographic waveform detected by an electrocardiographic waveform detecting device 60 of the apparatus of FIG. 7.

FIG. 7 shows a blood pressure monitor apparatus 8 which is different from the apparatus shown in FIG. 1 in that the former apparatus 8 additionally includes an electrocardiographic waveform detecting device 60. The electrocardiographic waveform detecting device 60 continuously detects an electrocardiographic waveform indicating the change of electric potential of the cardiac muscle of a living subject, through a plurality of electrodes 62 which are put on predetermined portions of the subject. Thus, the detecting device 60 provides a so-called electrocardiogram or ECG, and supplies an electric signal representative of the detected waveform to an electronic control device 28. In FIG. 8, a waveform shown in an upper portion thereof illustrates an example of the electrocardiographic waveform detected by the electrocardiographic waveform detecting device 60, and a waveform shown in a lower portion thereof illustrates an example of a pressure pulse wave detected by a pressure pulse wave sensor 46.

Figure 9:
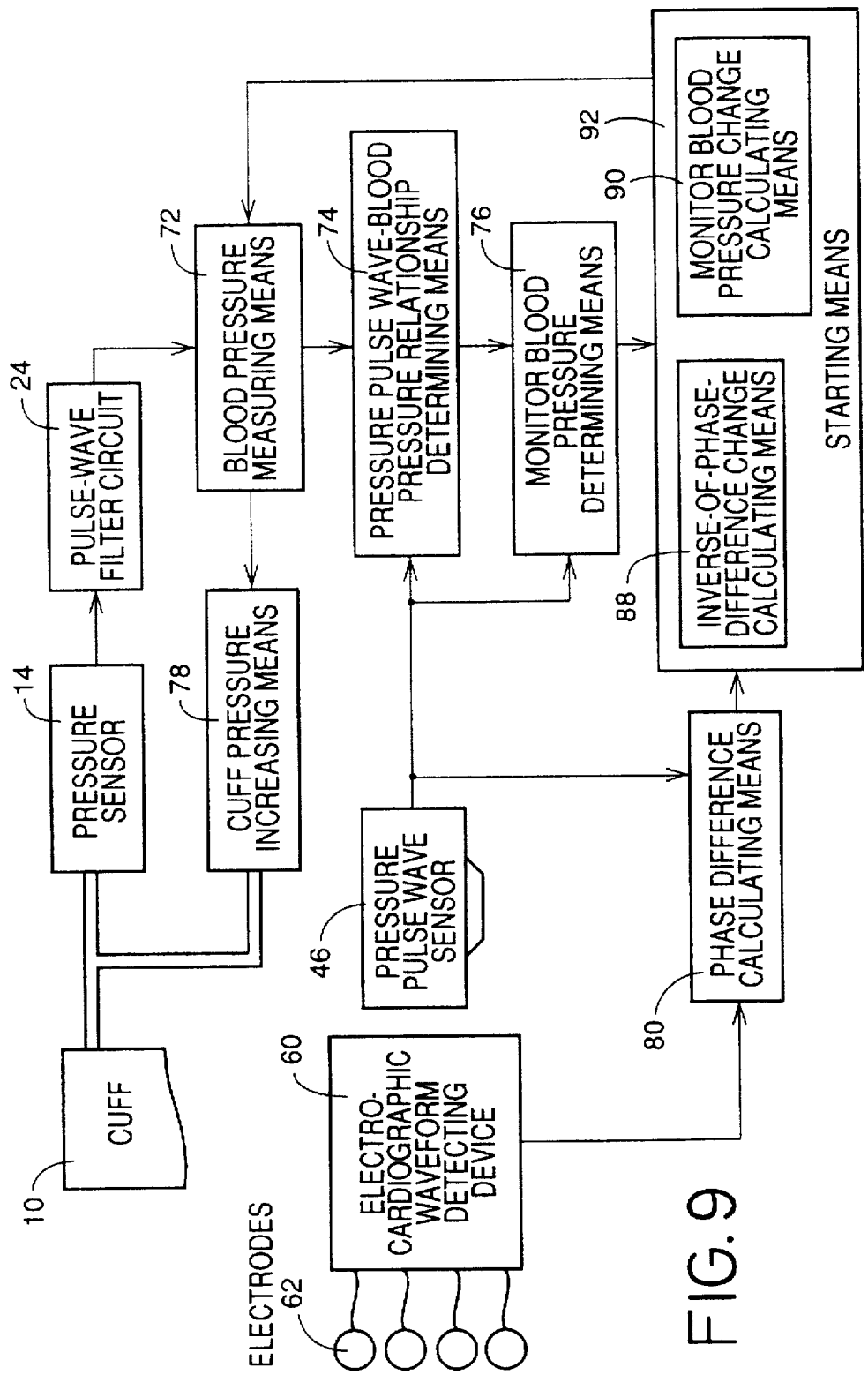
FIG. 9 is a block diagram for explaining various functions of a control device 28 of the apparatus of FIG. 7.

FIG. 9 is a block diagram for explaining essential functions of the electronic control device 28 of the blood pressure monitor apparatus 8. In the figure, a blood pressure measuring means 72 measures a systolic and a diastolic blood pressure value $BP_{SYS}$, $BP_{DIA}$, of a patient, according to an oscillometric method, based on the variation of respective magnitudes of pulses of a cuff pulse wave obtained as the pressure oscillation produced in a cuff 10 while the pressure of the cuff 10 is slowly changed. The pressure pulse wave sensor 46 is pressed on a body portion of the patient, such as a wrist 42, which is downstream of the body portion on which the cuff 10 is worn, such as an upper arm 12, and detects a pressure pulse wave produced from a radial artery 56 of the wrist 42. A pressure pulse wave-blood pressure relationship determining means 74 determines, in advance, a relationship between magnitude $P_M$ of pressure pulse wave and blood pressure value BP, based on the pressure pulse wave detected by the pressure pulse wave sensor 46 and the blood pressure measured by the blood pressure measuring means 72, for an individual patient. This relationship may be one shown in FIG. 3 and be defined by the following expression: $BP = A \cdot P_M + B$, where A is a constant indicative of the slope and B is a constant indicative of the intercept.

A monitor blood pressure determining means 76 successively determines, according to the relationship, a systolic and a diastolic blood pressure value $MBP_{SYS}$, $MBP_{DIA}$ (monitor blood pressure values), based on magnitudes $P_M$ of each pulse of the pressure pulse wave detected by the pressure pulse wave sensor 46, that is, maximum (upper-peak) and minimum (lower-peak) magnitudes $P_{Mmax}$, $P_{Mmin}$ of each pulse of the pressure pulse wave, and successively outputs the detected monitor blood pressure values to a display device 32. A cuff-pressure increasing means 78 changes the pressing pressure of the cuff 10 in a well known procedure during each blood pressure measuring operation of the blood pressure measuring means 72 that is started at a predetermined period for updating the relationship. For example, the cuff pressure increasing means 78 increases the pressure of the cuff 10 up to a predetermined target value about 180 mmHg which is higher than a systolic blood pressure of the patient, and then slowly decreases it at about 3 mmHg/sec while the blood pressure measurement algorithm is carried out. Upon termination of the blood pressure measurement, the cuff-pressure increasing means 78 releases the pressure of the cuff 10.

A phase difference calculating means 80 successively calculates a phase difference $T_d$ between a pressure pulse wave detected by the pressure pulse sensor 46 and an electrocardiographic waveform detected by the electrocardiographic waveform detecting device 60. As shown in FIG. 8, the phase difference $T_d$ is obtained as the time difference between an R wave of the electrocardiographic waveform and a maximum of differentiated waveform of the pressure pulse wave. A starting means 92 consists of an inverse-of-phase-difference change calculating means 88 and a monitor blood pressure change calculating means 90. More specifically described, the inverse-of-phase-difference change calculating means 88 successively calculates a change, $\Delta T_d^{-1}$, of respective inverses, $T_d^{-1}$, of the phase differences $T_d$ calculated by the phase difference calculating means 80. The change $\Delta T_d^{-1}$ may be the ratio, $(T_d^{-1} - T_d^{-1}{}_{AV})/T_d^{-1}{}_{AV}$, of the difference between the inverse $T_d^{-1}$ of a current phase difference $T_d$ and a current moving average $T_d^{-1}{}_{AV}\{=T_d^{-1}{}_{i-n}+\ldots+T_d^{-1}{}_{i-1}+T_d^{-1}/(n+1)\}$, to the moving average $T_d^{-1}{}_{AV}$.

The monitor blood pressure change calculating means 90 successively calculates a change, $\Delta MBP_{SYS}$, of systolic blood pressure values $MBP_{SYS}$ determined by the monitor blood pressure determining means 76. The change $\Delta MBP_{SYS}$ may be the ratio, $[MBP_{SYS} - (MBP_{SYS})_{AV}]/(MBP_{SYS})_{AV}$, of the difference between a current systolic blood pressure value $MBP_{SYS}$ and a current moving average, $(MBP_{SYS})_{AV}\{=(MBP_{SYS})_{i-n}+\ldots+(MBP_{SYS})_{i-1}+(MBP_{SYS})/(n+1)\}$, to the moving average. The starting means 92 calculates a comparison value $C_{DM}$ based on a change $\Delta T_d^{-1}$ of respective inverses of the phase differences calculated by the inverse-of-phase-difference change calculating means 88 and a change $\Delta MBP_{SYS}$ of the systolic blood pressure values calculated by the monitor blood pressure change calculating means 90, and starts a blood pressure measurement using the cuff 10 by the blood pressure measuring device 72, when the comparison value $C_{DM}$ is greater than a reference value $\alpha$. The comparison value $C_{DM}$ may be the the difference $|\Delta T_d^{-1} - \Delta MBP_{SYS}|$ between the change $\Delta T_d^{-1}$ and the change $\Delta MBP_{SYS}$, or the ratio $|\Delta T_d^{-1}/\Delta MBP_{SYS}|$ of the change $\Delta MBP_{SYS}$ to the change $\Delta T_d^{-1}$.

Figure 10:
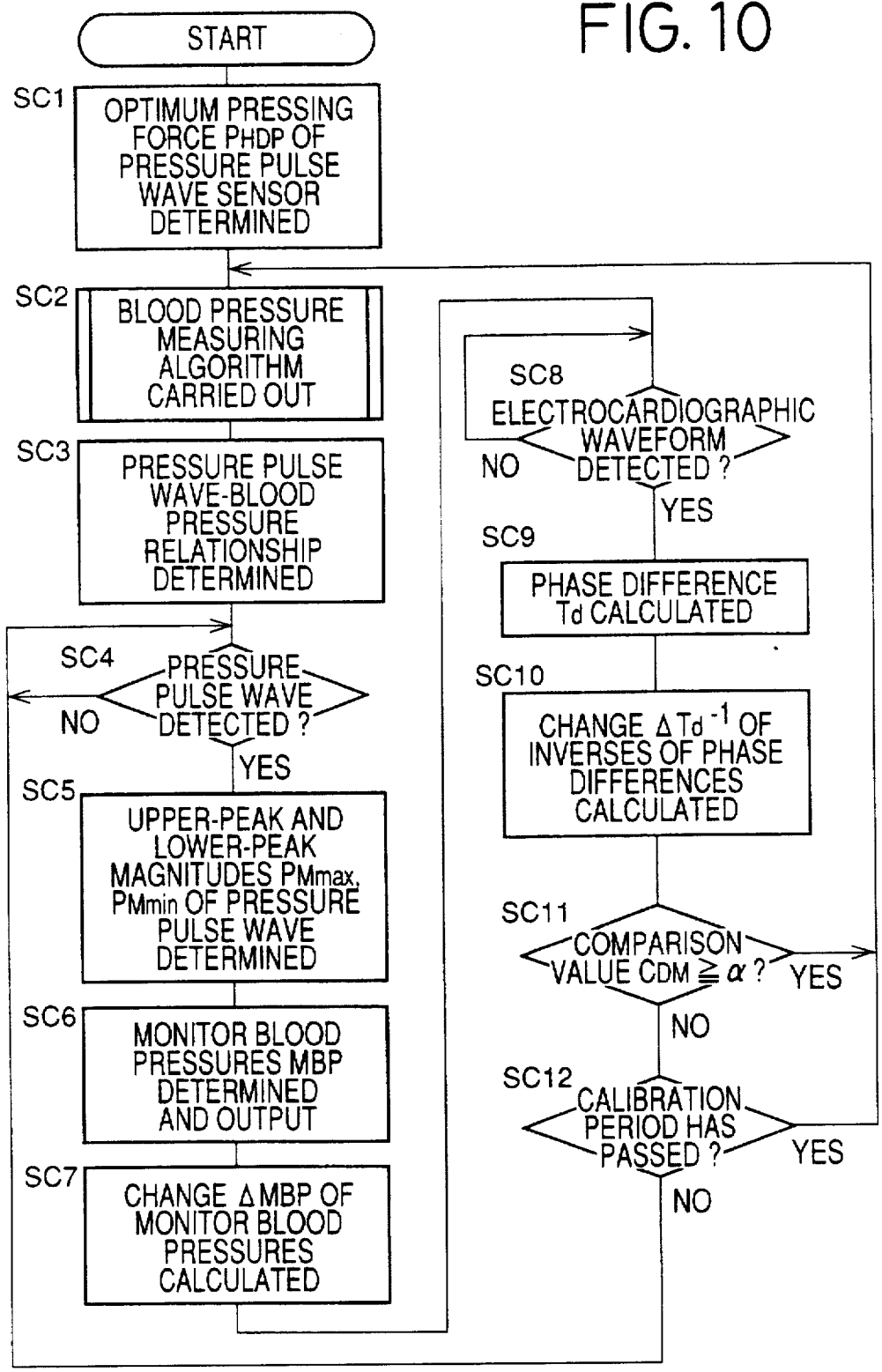
FIG. 10 is a flow chart representing the operation of the control device 28 of the apparatus of FIG. 7.

FIG. 10 is a flow chart representing the operation of the electronic control device 28 of the present blood pressure monitor apparatus 8. At Step SC1, a CPU 29 determines, as an optimum pressing force $P_{HDP}$ of the pressure pulse wave sensor 46, a pressure in a pressure chamber 48 when the respective amplitudes of pulses of the pressure pulse wave successively detected by the pressure pulse wave sensor 46 become maximum while the pressure of the pressure chamber 48 is slowly increased. With the pressure of the chamber 48 being held at the optimum pressing force $P_{HDP}$, the pressure pulse wave sensor 46 is pressed on a body surface 38 with the constant, optimum pressing force $P_{HDP}$.

Step SC1 is followed by Step SC2, corresponding to the blood pressure measuring means 72, to carry out a blood pressure measuring algorithm. That is, a selector valve 16 is switched to a cuff-inflation position, and an air pump 18 is operated to increase the cuff pressure up to a predetermined target value which is higher than an estimated systolic blood pressure of the patient (for example, 180 mmHg). Then, the air pump 18 is stopped and the selector valve 16 is switched to a slow-deflation position in which the selector valve 16 permits the pressurized air to be slowly discharged from the cuff 10. A systolic blood pressure value $BP_{SYS}$, a mean blood pressure value $BP_{MEAN}$, and a diastolic blood pressure value $BP_{DIA}$ are measured, according to a well known oscillometric type blood pressure determining algorithm, based on the variation of respective amplitudes of pulses of a pulse wave represented by a pulse wave signal $SM_1$ obtained while the cuff pressure is slowly decreased at a predetermined low rate of about 3 mmHg/sec, and a pulse rate is determined based on the interval of successive two pulses of the cuff pulse wave. The thus measured blood pressure values and pulse rate are displayed by a display device 32, and the selector valve 16 is switched to a quick-deflation position in which the selector valve 16 permits the pressurized air to be quickly discharged from the cuff 10.

Next, Step SC2 is followed by Step SC3, corresponding to the pressure pulse wave-blood pressure relationship determining means 74, to obtain a relationship between magnitude $P_M$ of pressure pulse wave and blood pressure, shown in FIG. 3, based on the pressure pulse wave detected by the pressure pulse wave sensor 46 (absolute value, that is, magnitude of pulse wave signal $SM_2$) and the blood pressure values $BP_{SYS}$, $BP_{DIA}$ measured using the cuff 10 at Step SC2. More specifically described, one heartbeat-synchronous pulse of the pressure pulse wave detected by the pressure pulse wave sensor 46 is read in by the CPU 29, and an upper-peak magnitude $P_{Mmax}$ and a lower-peak magnitude $P_{Mmin}$ of the one pulse are determined by the CPU 29. Then, the relationship between magnitude of pressure pulse wave and blood pressure is determined, based on the upper-peak and lower-peak magnitudes $P_{Mmax}$, $P_{Mmin}$ of the pressure pulse wave and the systolic and diastolic blood pressure values $BP_{SYS}$, $BP_{DIA}$ measured at Step SC2.

Step SC3 is followed by Step SC4 to judge whether or not one pulse of the pressure pulse wave has been detected. If the judgment at Step SC4 is negative, the control of the CPU 29 waits until a positive judgment is made. If the judgment at Step SC4 is positive, the control of the CPU 29 goes to Steps SC5 and SC6 corresponding to the monitor blood pressure determining means 76. At Step SC5, the CPU 29 determines a maximum magnitude $P_{Mmax}$ (upper-peak magnitude) and a minimum magnitude $P_{Mmin}$ (lower-peak magnitude) of the one pulse of the pressure pulse wave detected by the pressure pulse wave sensor 46 pressed at the optimum pressing force $P_{HDP}$. Step SC5 is followed by Step SC6 to determine a systolic and a diastolic blood pressure value $BP_{SYS}$, $BP_{DIA}$ (monitor blood pressure values) based on the maximum and minimum magnitudes $P_{Mmax}$, $P_{Mmin}$ of the pressure pulse wave according to the pressure pulse wave-blood pressure relationship determined at Step SC3, and control the display device 32 to display the determined monitor blood pressure values together with a continuous waveform of the pressure pulse wave.

Subsequently, the control of the CPU 29 goes to Step SC7, corresponding to the monitor blood pressure change calculating means 90, so as to calculate a change $\Delta MBP_{SYS}$ of the systolic blood pressure values $MBP_{SYS}$. More specifically described, the CPU 29 calculates the ratio $[MBP_{SYS}-(MBP_{SYS})_{AV}]/(MBP_{SYS})_{AV}$ of the difference between the current systolic blood pressure $MBP_{SYS}$ and the current moving average $(MBP_{SYS})_{AV}[=(MBP_{SYS})_{i-n}+\ldots+(MBP_{SYS})_{i-1}+(MBP_{SYS})/(n+1)]$ to the moving average.

Step SC7 is followed by Step SC8 to judge whether or not one pulse of the electrocardiographic waveform has been input. If the judgment at Step SC8 is negative, the control of the CPU 29 waits for one pulse to be input. If the judgment at Step SC8 is positive, the control of the CPU 29 goes to Step SC9 corresponding to the phase difference calculating means 80. At Step SC9, the CPU 29 calculates the phase difference $T_d$ between the one pulse of the pressure pulse wave and the one pulse of the electrocardiographic waveform. The phase difference $T_d$ is calculated as the time difference between the time of occurrence of the R wave of the one pulse of electrocardiographic waveform and the time of occurrence of the maximum of the differentiated waveform of pressure pulse wave, as shown in FIG. 8. Step SC9 is followed by Step SC10, corresponding to the inverse-of-phase-difference change calculating means 88, to calculate the change $\Delta T_d^{-1}$ of respective inverses of the phase differences $T_d^{-1}$. That is, at Step SC10, the ratio $(T_d^{-1}-T_d^{-1}{}_{AV})/T_d^{-1}{}_{AV}$ of the difference between the inverse of current phase difference and the current moving average $T_d^{-1}{}_{AV}[=T_d^{-i-n+}\ldots+T_d^{-1}{}_{i-1}+T_d^{-1}/(n+1)]$ to the moving average.

Step SC10 is followed by Step SC11 corresponding to the starting means 92. At Step SC11, the CPU 29 calculates, as the above-mentioned comparison value $C_{DM}$, the difference $|\Delta T_d^{-1}-\Delta MBP_{SYS}|$ between the value $\Delta T_d^{-1}$ and the value $\Delta MBP_{SYS}$, or the ratio $|\Delta T_d^{-1}/\Delta MBP_{SYS}|$ of the value $\Delta MBP_{SYS}$ to the value $\Delta T_d^{-1}$, and judges whether or not the comparison value $C_{DM}$ is greater than a reference value $\alpha$. The reference value $\alpha$ is used as a criterion for judging whether the blood pressure of the patient has unusually changed. If the judgment at Step SC11 is positive, the control of the CPU 29 goes back to Step SC2 to update the pressure pulse wave-blood pressure relationship, since the reliability of the monitor blood pressure values MBP is doubtful. On the other hand, if the judgment at Step SC11 is negative, the CPU goes to SC12 since the monitor blood pressure values MBP is reliable.

At Step SC12, the CPU 29 judges whether or not a predetermined period of about 30 minutes has passed after the last blood pressure measurement using the cuff 10 is carried out at Step SC2. That is, the CPU 29 judges whether or not a calibration period has passed. If the judgment at Step SC12 is negative, Steps SC4 to SC11 are repeated and systolic and diastolic blood pressure values $MBP_{SYS}$, $MBP_{DIA}$ are continuously determined and displayed based on each of heartbeat-synchronous pulses of the pressure pulse wave. On the other hand, if the judgment at Step SC12 is positive, the control of the CPU 29 goes to back to Step SC2 and the following steps to update the relationship.

In the present embodiment, an electrocardiographic waveform of a living subject is detected at Step SC8 by the electrocardiographic waveform detecting device 60, and a pressure pulse wave produced from an artery of the subject is detected at Step SC4, so that a phase difference $T_d$ between the phase of the pressure pulse wave and that of the electrocardiographic waveform is calculated at Step SC9 corresponding to the phase difference calculating means 80. The change $\Delta T_d^{-1}$ of respective inverses of the phase differences $T_d^{-1}$ is calculated at Step SC10 corresponding to the inverse-of-phase-difference change calculating means 88. A monitor blood pressure value MBP is determined at Step SC6 corresponding to the monitor blood pressure determining means 76 based on the pressure pulse wave, and a change $\Delta MBP_{SYS}$ of the monitor systolic blood pressure values $MBP_{SYS}$ is calculated at Step SC7 corresponding to the monitor blood pressure change calculating means 90. If the comparison value $C_{DM}$ based on the change $\Delta T_d^{-1}$ and the change $\Delta MBP_{SYS}$, for example, the difference or ratio of the two changes, is greater than a predetermined reference value $\alpha$, the starting means 92 controls the blood pressure measuring means 72 to start a blood pressure measurement using the cuff 10. It has experimentally been found that the change of the monitor blood pressure values MBP is proportional to the change of the respective inverses of phase differences calculated from the electrocardiographic wave and the pressure pulse wave. If the comparison value $C_{DM}$ based on the changes $\Delta T_d^{-1}$, $\Delta MBP_{SYS}$ is greater than the reference value $\alpha$, that is, if the change of the monitor blood pressure values MBP is not proportional to the change of the respective inverses of phase differences calculated from the electrocardiographic wave and the pressure pulse wave, the CPU 29 judges that the reliability of the monitor blood pressure values is doubtful and starts a blood pressure measurement with the cuff 10. Consequently the calibration period at which each blood pressure measurement using the cuff 10 is carried out for updating the pressure pulse wave-blood pressure relationship may be pre-selected at a considerably long time. Therefore, the frequency of blood pressure measurements using the cuff 10 is decreased and the discomfort of the living subject is reduced. In addition, the length of each continuous blood pressure monitoring operation is maximized.

Furthermore, since in the present embodiment Step SC12 is provided, the relationship between magnitude of pressure pulse wave and monitor blood pressure value MBP is updated at the predetermined calibration period. Thus, the accuracy of monitor blood pressure values MBP determined based on the pressure pulse wave detected by the pressure pulse wave sensor 46 is maintained.

There will be described another embodiment according to the present invention. Hereinafter, the same parts as those of the prior embodiments are denoted by the same reference numerals and the detail description thereof is omitted.

Figure 11:
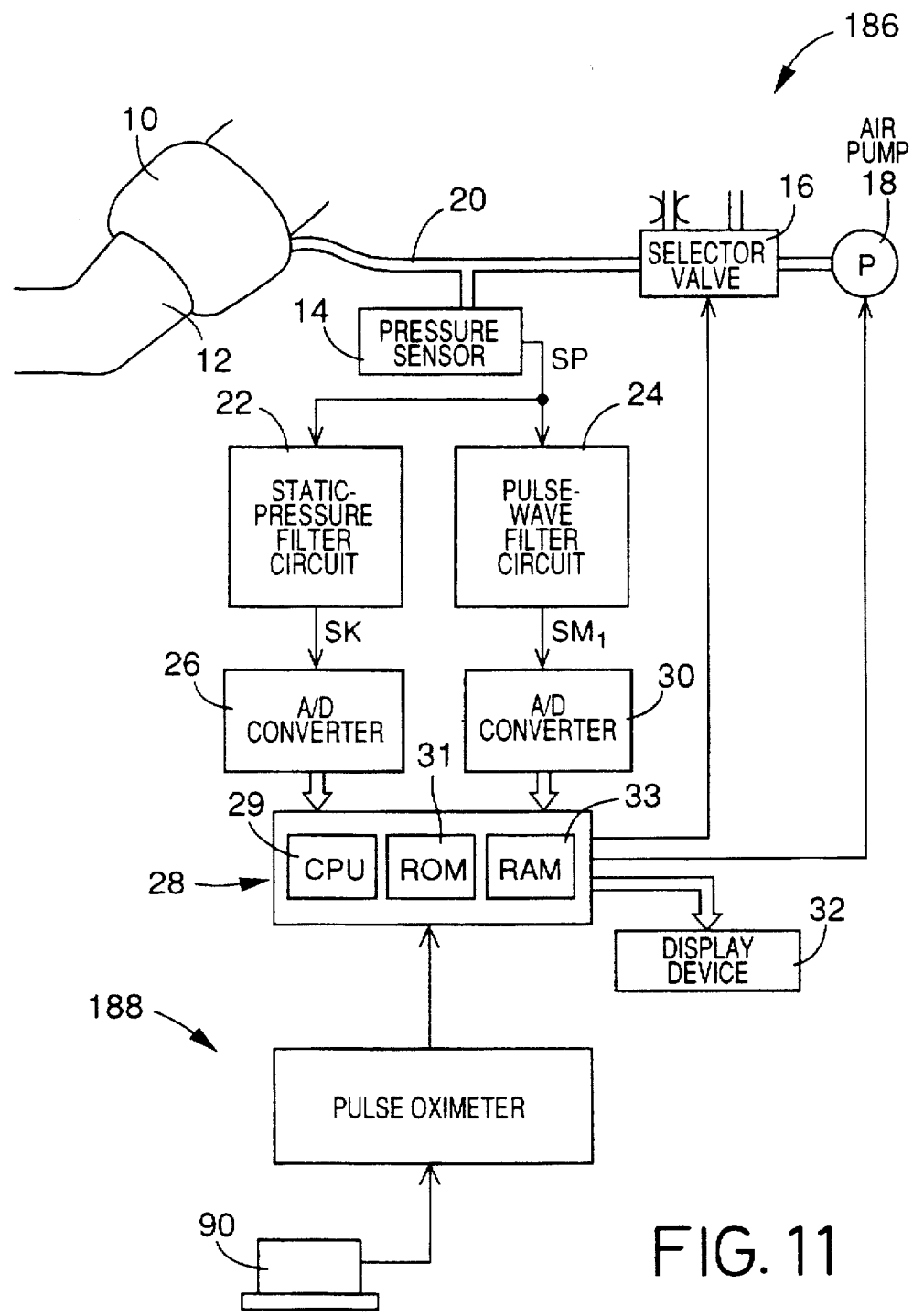
FIG. 11 is a diagrammatic view corresponding to FIG. 1, showing a blood pressure monitor apparatus as yet another embodiment according to the present invention.

FIG. 11 shows a blood pressure monitor apparatus 186 to which the invention is applied. As shown in the figure, the blood pressure monitor apparatus 186 is different from the apparatus 8 shown in FIG. 8 in that the former apparatus 186 utilizes a photoelectric pulse wave detected by a pulse oximeter 188.

Figure 12:
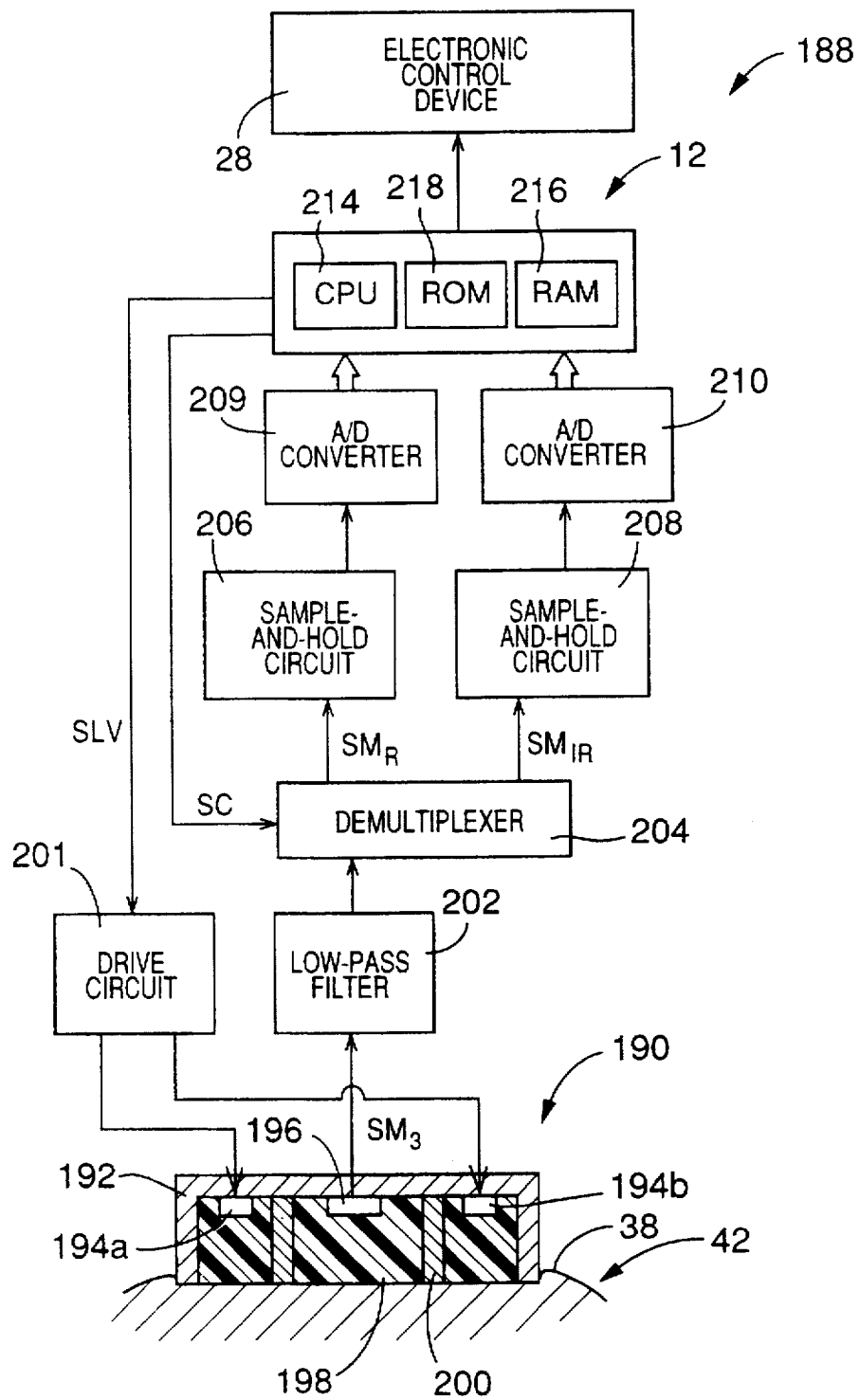
FIG. 12 is a diagrammatic view for illustrating the construction of a pulse oximeter of the apparatus of FIG. 11.

The pulse oximeter 188 includes a photoelectric pulse wave detecting probe 190 for measuring an oxygen saturation (hereinafter, referred to as the "probe"). As shown in FIG. 12, the probe 190 is worn on a body surface 38 of a body portion of a patient, such as the forehead of the patient, which is different from an upper arm 12 on which a cuff 10 is worn. The probe 190 is held in close contact with the body surface 38 with the help of fastening bands (not shown). The probe 190 includes a container-like housing 192 which opens in a certain direction, a first and a second light-emitting element 194a, 194b, such as LEDs, which are disposed on a peripheral portion of an inner bottom surface of the housing 192 (hereinafter, referred to as the light-emitting elements 194 in the case where the first and second light emitting elements 194a, 194b are not discriminated from each other), a light-receiving element 196, such as a photodiode or a phototransister, which is disposed on a central portion of the inner bottom surface of the housing 192, a transparent resin 198 which is integrally disposed in the housing 192 to cover the light-emitting elements 194 and the light-receiving element 196, and an annular shade member 200 which is disposed between the light-emitting elements 194 and the light-receiving element 196, for preventing the lights emitted toward the body surface 38 by the light-emitting elements 194 and reflected from the body surface 38, from being received by the light-receiving element 196.

The first and second light-emitting elements 194a, 194b emit a red light having about 660 nm wavelength and an infrared light having about 800 nm wavelength, respectively. The first and second light-emitting elements 194a, 194b alternately emit the lights at a predetermined frequency according to respective drive currents supplied thereto from a drive circuit 201. A portion of each of the lights emitted toward the body surface 38 by the light-emitting elements 194 is reflected from a body portion of the patient where capillaries are close together, and is received by the light-receiving element 196.

The light-receiving element 196 outputs, through a low-pass filter 202, a photoelectric pulse wave signal $SM_3$ representative of an amount of received light. The light-receiving element 196 is connected to the low-pass filter 202 via an amplifier or the like. The low-pass filter 202 eliminates noise having frequencies higher than that of a pulse wave, from the photoelectric pulse wave signal $SM_3$ input thereto, and outputs the signal $SM_3$ from which the noise has been eliminated, to a demultiplexer 204. The demultiplexer 204 is alternately switched according to signals which are supplied thereto from an electronic control device 28 in synchronism with the light emissions of the first and second emitting elements 194a, 194b. Thus, the demultiplexer 204 successively supplies, to an I/O port (not shown) of an electronic control device 212, an electric signal $SM_R$ representative of the red light through a sample-and-hold circuit 206 and an A/D converter 109, and an electric signal $SM_{IR}$ representative of the infrared light through a sample-and-hold circuit 208 and an A/D converter 210. The sample-and-hold circuits 206, 208 hold the current signals $SM_R$, $SM_{IR}$ input thereto, respectively, and do not output the signals to the A/D converters 209, 210, respectively, until the prior signals $SM_R$, $SM_{IR}$ are completely converted by the A/D converters 209, 210, respectively. The control device 212 is connected to a display device (not shown) which displays a measured blood oxygen saturation.

The control device 212 is provided by a microcomputer which includes a CPU 214, a RAM 216, a ROM 218, etc. and is capable of mutually communicating with the control device 28. The CPU 214 carries out a measuring operation according to control programs pre-stored in the ROM 218 by utilizing a temporary-storage function of the RAM 216, and calculates an oxygen saturation based on the electric signals $SM_R$, $SM_{IR}$. The oxygen saturation is displayed by the display device. Furthermore, the CPU 214 successively supplies the signals $SM_R$ and $SM_{IR}$ to the control device 28.

An oxygen saturation is calculated based on an actual ratio, $\{(V_{dR}-V_{SR})/(V_{dR}+V_{SR})\}/\{(V_{dIR}-V_{SIR})/(V_{dIR}+V_{SIR})\}$, according to a predetermined relationship between oxygen saturation and the ratio, as disclosed in U.S. Pat. No. 5,131,391 filed by the assignee of the present application. In the above expression $V_{dR}$, $V_{SR}$ represent an upper-peak magnitude and a lower-peak magnitude of the waveform of photoelectric pulse wave indicative of the read light, respectively, and $V_{dIR}$, $V_{SIR}$ represent an upper-peak magnitude and a lower-peak magnitude of the waveform of photoelectric pulse wave indicative of the infrared right, respectively. $(V_{dR}-V_{SR})$ or $(V_{dIR}-V_{SIR})$ represents the amplitude of AC component of the waveform of each photoelectric pulse wave. $(V_{dR}+V_{SR})$ or $(V_{dIR}+V_{SIR})$ represents twice the magnitude of DC component of the waveform of each photoelectric pulse wave. A photoelectric pulse wave has a curve similar to a pressure pulse wave shown in an upper portion of FIG. 2.

Figure 13:
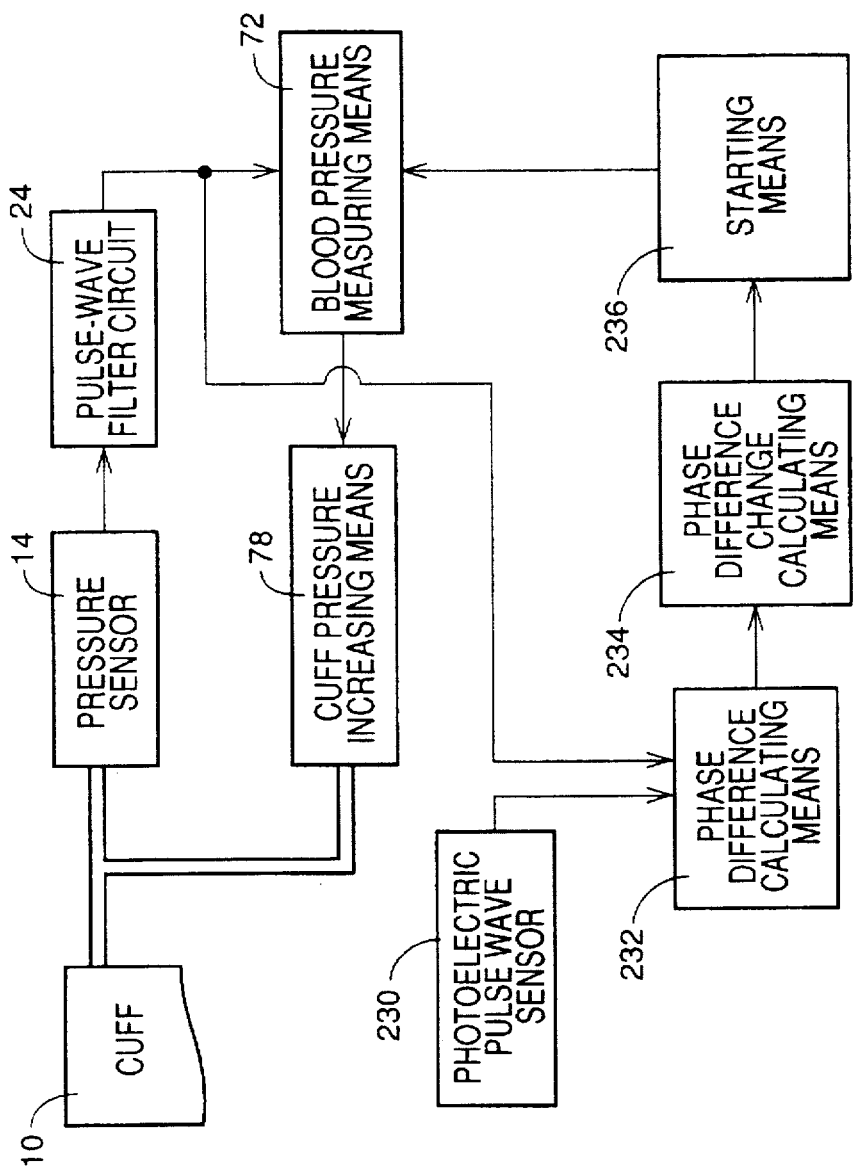
FIG. 13 is a block diagram for explaining various functions of a control device of the apparatus of FIG. 11.

FIG. 13 is a block diagram for illustrating essential functions of the electronic control device 212 of the blood pressure monitor apparatus 186 constructed as described above. In this figure, a blood pressure measuring means 72 carries out a well known blood pressure measurement using a cuff 10 at a predetermined period and updates the blood pressure values being displayed. A cuff-pressure increasing means 78 increases the pressure of the cuff 10 up to a predetermined value at a predetermined period, while the blood pressure measuring means 72 is not operated. A photoelectric pulse wave sensor 230 corresponding to the prove 190 detects a photoelectric pulse wave from a surface of a body portion different from the body portion on which the cuff 10 is worn. In the present embodiment, the photoelectric pulse wave sensor 230 functions as the other of a pair of heartbeat-synchronous wave sensors which detects a photoelectric pulse wave as a sort of heartbeat-synchronous wave.

A phase difference calculating means 232 successively calculates a phase difference $D_{CK}$ between a photoelectric pulse wave detected by the photoelectric pulse wave sensor 230 and a cuff pulse wave detected as a pressure oscillation produced in the cuff 10 which is inflated by the cuff-pressure increasing means 78 during a non-blood-pressure-measurement period. In the present embodiment, a pulse wave signal $SM_1$ which is output from a pulse-wave filter circuit 24 represents a cuff pulse wave as an oscillatory pressure wave which is produced from a brachial artery (not shown) of the patient in synchronism with the heartbeat of the patient and is propagated to the cuff 10. The cuff 10, pressure sensor 14, and pulse-wave filter circuit 24 cooperate with one another to function as one of the pair of heartbeat-synchronous wave sensors which detects the cuff pulse wave as a sort of heartbeat-synchronous wave.

A phase difference change calculating means 234 calculates a change $\Delta D$ of the phase differences $D_{CK}$ successively calculated by the phase difference calculating means 232. The change $\Delta D$ may be a moving average $D_{AV}$ of the phase differences $D_{CK}$, or the ratio or amount of change of a current phase difference $D_{CK}$ from a phase difference $D_{CKM}$ calculated in the prior blood pressure measurement. A starting means 236 starts a blood pressure measurement of the blood pressure measuring device 72, when a change $\Delta D$ of phase differences $D_{CK}$ calculated by the phase difference change calculating means 234 is greater than a reference value $\beta$.

FIG. 14 is a flow chart representing the operation of the control device 212 of the blood pressure monitor apparatus 86. At Step SB1, the CPU 29 reads in photoelectric pulse wave signals supplied from the control device 212 of the pulse oximeter 88. Step SB1 is followed by Step SB2 to judge whether or not a predetermined interval-check period $T_{INT}$ has passed after the prior interval check is carried out at Steps SB4 and the following steps. The interval-check period is selected from, e.g., several tens of seconds to several minutes.

If the judgement at Step SB2 is negative, the control of the CPU 29 goes to Step SB3 to judge whether or not a predetermined blood pressure measurement period $T_B$ has passed after the prior blood pressure measurement using the cuff 10 is carried out at Step SB8. The blood pressure measurement period $T_B$ is set at a considerably long time, e.g., several minutes to several tens of minutes, for example. If the judgement at Step SB3 is negative, this routine is terminated and the control of the CPU 29 returns to Step SB1. On the other hand, the judgement at Step SB3 is positive, the control of the CPU 29 goes to Step SB8, corresponding to the blood pressure measuring device 72, to carry out a blood pressure measurement using the cuff 10, according to an oscillometric method. Thus, a systolic and a diastolic blood pressure values $BP_{SYS}$, $BP_{DIA}$ of the patient are measured and displayed. Then, this routine is terminated.

If the judgement at Step SB2 is positive, the control of the CPU 29 goes to Step SB4, corresponding to the cuff-pressure increasing means 78, to increase the pressure of the cuff 10 up to a predetermined value during a non-blood-pressure-measurement period when Step SB8 is not carried out. The predetermined value is set at a value not higher than a mean blood pressure of the living subject, preferably, not higher than a minimum blood pressure of the subject.

Step SB4 is followed by Step SB5, corresponding to the phase difference calculating means 232, to calculate a phase difference $D_{CK}$ between a photoelectric pulse wave and a cuff pulse wave. For example, as shown in FIG. 15, the phase difference $D_{CK}$ is calculated as a time difference between an upper peak of one heartbeat-synchronous pulse of the photoelectric pulse wave and an upper peak of a corresponding heartbeat-synchronous pulse of the cuff pulse wave. Step SB5 is followed by Step SB6, corresponding to the phase difference change calculating means 234, to calculate a change $\Delta D$ of the phase differences $D_{CK}$. The change $\Delta D$ may be the amount, $(D_{CK}-D_{AV})$, of change of the current phase difference $D_{CK}$ from the current moving average $D_{AV}[=D_{CKi-n}+ \ldots +D_{CKi-1}+D_{CKi}/(n+1)]$, the rate, $(D_{CK}-D_{AV})/D_{AV}$, of change of the current phase difference $D_{CK}$ from the current moving average $D_{AV}$, the amount, $(D_{CK}-D_{CKM})$, of change of the current phase difference $D_{CK}$ from the phase difference $D_{CKM}$ calculated in the prior blood pressure measurement using the cuff, or the rate, $(D_{CK}-D_{CKM})/D_{CKM}$, of change of the current phase difference $D_{CK}$ from the phase difference $D_{CKM}$.

Step SB6 is followed by Step SB7, corresponding to the starting means 236, to judge whether or not the change $\Delta D$ of the phase differences is greater than a reference value $\beta$. The reference value $\beta$ is experimentally obtained in advance and is used as a criterion for judging whether the blood pressure of the patient has unusually changed.

If the judgment at Step SB7 is negative, that is, the blood pressure of the patient are stable, the control of the CPU 29 goes to Step SB3, without going to Step SB8 to carry out a blood pressure measurement using the cuff 10. On the other hand, if the judgment at Step SB7 is positive, that is, if the blood pressure of the patient has unusually changed, the control of the CPU 29 goes to Step SB8 to start a blood pressure measurement using the cuff 10.

In the above-mentioned embodiment, a phase difference $D_{CK}$ between a cuff pulse wave and a photoelectric pulse wave is calculated at Step SB5 corresponding to the phase difference calculating means 232, and a change $\Delta D$ of the phase differences $D_{CK}$ is calculated at Step SB6 corresponding to the phase difference change calculating means 234. At Step SB7 corresponding to the starting means 236, a blood pressure measurement at Step SB8 corresponding to the blood pressure measuring device 72 is started if the change $\Delta D$ of the phase differences $D_{CK}$ is greater than the reference value $\beta$. Thus, so long as the change $\Delta D$ of the phase differences is not greater than the reference value $\beta$, that is, while the blood pressure of the patient is stable, no blood pressure measurement using the cuff 10 is carried out, so that the frequency of blood pressure measurements using the cuff 10 is decreased and the discomfort of the living subject is reduced.

In the present embodiment, there is no need to provide an exclusive pair of heartbeat-synchronous wave sensors for obtaining a phase difference, since a phase difference $D_{CK}$ is calculated from the cuff pulse wave detected as the pressure oscillation in the cuff 10 provided for the blood pressure measurements and the photoelectric pulse wave detected by the photoelectric pulse wave detecting probe 190 provided for the blood oxygen saturation measurements.

In the present embodiment, at Step SB4 corresponding to the cuff-pressure increasing means 78, the pressure of the cuff 10 is increased, at a predetermined period, to a predetermined value which is not higher than a mean blood pressure of the patient, preferably, a diastolic blood pressure of the patient, while the blood pressure measurements are not carried out. Thus, the pressure of the cuff 10 is kept low while the pulse wave is detected for calculating phase differences and the discomfort of the patient is accordingly reduced.

While the present invention has been described in its preferred embodiments by reference to the drawings, it is to be understood that the invention may otherwise be embodied.

In the illustrated embodiments, the cuff 10 employed for the blood pressure measurements, the pressure pulse wave sensor 46 for the blood pressure monitoring, or the photoelectric pulse wave detecting probe 190 for the blood oxygen saturation measurements is utilized for detecting a pulse wave based on which a phase difference $D_{CP}$ or $D_{CK}$ is calculated. However, another pair of heartbeat-synchronous wave sensors, that is, a pair of pulse wave sensors may independently be employed by each blood pressure monitor apparatus. The pair of pulse wave sensors are worn on different body portions of the patient, respectively.

While, in the embodiment shown in FIG. 1, the cuff 10, pressure sensor 14, and the pulse-wave filter circuit 24 are used as one of the pair of heartbeat-synchronous wave sensors which detects the cuff pulse wave as a sort of heartbeat-synchronous wave, an electrocardiographic waveform detecting device which detects an electrocardiographic waveform through electrodes being put on a body surface of a living subject may be employed as one of the pair of heartbeat-synchronous wave sensors. Since an R wave of the electrocardiographic waveform substantially corresponds to a lower peak of an aortic pressure pulse wave, a time difference between the R wave of the electrocardiographic waveform and the cuff pulse wave, photoelectric pulse wave, or pressure pulse wave may be detected as a phase difference. In the latter case, the absolute value of the phase difference is considerably large and the accuracy of calculation of phase differences is accordingly improved.

While in the illustrated embodiments the blood pressure measuring means 72 determines blood pressure values based on the change in magnitude of the pulse wave detected with the change of the pressure of the cuff 10, according to the so-called oscillometric method, it is possible to determine blood pressure values based on Korotkoff-sounds which occur and disappear with the change of the pressure of the cuff 10, according the so-called Korotkoff-sound method.

While, at Step SA4 of FIG. 6, the ratio $|D_M - D_{CP}|/D_{CP}$ of the difference $(D_M - D_{CP})$ to the phase difference $D_{CP}$ is used as the difference between the phase difference $D_M$ calculated based on a monitor blood pressure value MBP when the inflation of the cuff 10 starts, and the phase difference $D_{CP}$ obtained at Step SA3. However, the difference $(D_M - D_{CP})$ itself may be used without being divided by the phase difference $D_{CP}$.

In the embodiment shown in FIG. 7, the inverse $T_d^{-1}$ of phase difference is calculated based on the time difference $T_d$ between the R wave of electrocardiographic waveform and the time of maximum point of the differentiated waveform of pressure pulse wave. However, the time difference $T_d$ may otherwise be defined as the time difference between the R wave of electrocardiographic waveform and the time of maximum point of the pressure pulse wave, the time difference between the R wave of electrocardiographic waveform and the time of minimum point of pressure pulse wave, etc. In short, the time difference $T_d$ may be calculated as the time difference between the time of predetermined point on an electrocardiographic waveform and the time of predetermined point on a pressure pulse wave.

In the embodiment shown in FIG. 7, the change $\Delta MBP$ of monitor blood pressure values MBP is calculated as the change of systolic blood pressure values $MBP_{SYS}$. However, the change $\Delta MBP$ of monitor blood pressure values MBP may be calculated as the change of diastolic blood pressure values $MBP_{DIA}$. In short, the change $\Delta MBP$ of monitor blood pressure values MBP may be calculated as the change of values of predetermined monitor blood pressure MBP.

In the embodiment shown in FIG. 7, the change $\Delta T_d^{-1}$ of respective inverses $T_d^{-1}$ of phase differences or the change $\Delta MBP$ of monitor blood pressure values MBP is calculated as the rate of change of the current inverse $T_d^{-1}$ relative to the current moving average of respective inverses, or the rate of change of the current monitor blood pressure relative to the current moving average of respective monitor blood pressures, respectively. However, the change $\Delta T_d^{-1}$ or the change $\Delta MBP$ may be calculated as the rate of change of the current inverse $T_d^{-1}$ relative to a regression line of respective inverses $T_d^{-1}$ of the phase differences, or the rate of change of the current monitor blood pressure MBP relative to a regression line of respective monitor blood pressure values MBP, respectively. In short, any method in which the rate of change of the inverses $T_d^{-1}$ of phase differences or the rate of change of the monitor blood pressure values MBP is obtained with accuracy may be employed.

In the embodiment shown in FIG. 7, Step SC12 is provided to update the relationship at a predetermined calibration period. However, Step SC 12 may not be provided. In the latter case, Step SC4 and the following steps are repeated if the judgment Step S11 is negative. Thus, only when a monitor blood pressure value MBP determined based on the pressure pulse wave detected by the pressure pulse wave sensor 46 is doubtful, a blood pressure measurement using the cuff 10 is carried out for updating the relationship. Therefore, the discomfort of a patient is reduced much more and the degree of continuity of the blood pressure monitoring is improved much more.

In the embodiment shown in FIG. 11, the photoelectric pulse wave detecting probe 190 is of a reflection type which detects the lights reflected from the body surface 38 of a living subject. However, it is possible to employ a photoelectric pulse wave detecting probe of a transmission type which detects lights transmitted through the body tissue of a living subject.

A pulse wave sensor may be, e.g., an impedance sensor which detects the change of impedance of a living subject due to the pulsation of blood of the subject, according to a well known impedance plethysmography.

It is to be understood that the present invention may be embodied with other modifications without departing from the scope of the invention.

We claim:

1. A blood pressure monitor apparatus including a blood pressure measuring device for measuring a blood pressure value of a living subject based on variation of a pulse-synchronous wave obtained through a cuff adapted to be worn on the living subject by changing a pressure of the cuff, a pressure pulse wave sensor adapted to be pressed on an artery of the living subject for detecting a pressure pulse wave produced from the artery of the living subject, a pressure pulse wave-blood pressure relationship determining means for determining, at a predetermined period, a pressure pulse wave-blood pressure relationship between magnitude of pressure pulse wave and blood pressure, based on the pressure pulse wave detected by said pulse wave sensor and the blood pressure value measured by said blood pressure measuring device, by starting said blood pressure measuring device at said predetermined period, and a monitor blood pressure determining means for successively determining a monitor blood pressure value based on an actual pressure pulse wave detected by said pressure pulse wave sensor, according to said pressure pulse wave-blood pressure relationship, the blood pressure monitor apparatus being characterized by comprising:

a pair of heartbeat-synchronous wave sensors for detecting, on different portions of said living subject, respective heartbeat-synchronous waves produced in synchronism with a heartbeat of the living subject;

a phase difference calculating means for calculating a phase difference between one of the heartbeat-synchronous waves detected by one of said pair of heartbeat-synchronous wave sensors and the other of the heartbeat-synchronous waves detected by the other of said pair of heartbeat-synchronous wave sensors;

a phase difference-blood pressure relationship determining means for determining a phase difference-blood pressure relationship between phase difference and blood pressure, based on the phase difference calculated by said phase difference calculating means and the blood pressure value measured by said blood pressure measuring device; and a blood pressure measurement terminating means for terminating a blood pressure measurement of said blood pressure measuring device, when a difference between a phase difference obtained according to said phase difference-blood pressure relationship based on a monitor blood pressure value determined by said monitor blood pressure determining means, and a phase difference obtained by said phase difference calculating means, when the blood pressure measurement of said blood pressure measuring device starts, is smaller than a predetermined reference value.

2. A blood pressure monitor apparatus according to claim 1, wherein one of said pair of heartbeat-synchronous wave sensors includes said cuff, a pressure sensor for detecting a pressure of the cuff, and a band-pass filter for extracting, as one of said heartbeat-synchronous waves, a cuff pulse wave produced in synchronism with the heartbeat of the living subject, from the pressure of the cuff detected by the pressure sensor.

3. A blood pressure monitor apparatus according to claim 2, wherein said phase difference calculating means calculates said phase difference based on said cuff pulse wave detected from said cuff when an increasing of the pressure of said cuff is started by said blood pressure measuring device.

4. A blood pressure monitor apparatus according to claim 1, wherein the other of said pair of heartbeat-synchronous wave sensors includes said pressure pulse wave sensor.

5. A blood pressure monitor apparatus according to claim 1, wherein one of said pair of heartbeat-synchronous wave sensors includes an electrocardiographic waveform detecting device for detecting an electrocardiographic waveform through electrodes which are adapted to be applied to a surface of the living subject.

6. A blood pressure monitor apparatus including a blood pressure measuring device for measuring, at a predetermined period, a blood pressure value of a living subject based on variation of a pulse wave obtained through a cuff adapted to be worn on the living subject by changing a pressure of the cuff, the blood pressure monitor apparatus comprising:

a pair of heartbeat-synchronous wave sensors for detecting, on different portions of the living subject, respective heartbeat-synchronous waves produced in synchronism with a heartbeat of the living subject;

a phase difference calculating means for calculating a phase difference between one of the heartbeat-synchronous waves detected by one of said pair of heartbeat-synchronous wave sensors and the other of the heartbeat-synchronous waves detected by the other of said pair of heartbeat-synchronous wave sensors;

a phase difference change calculating means for calculating a change of the phase differences calculated by said phase difference calculating means; and a starting means for starting a blood pressure measurement of said blood pressure measuring device, when the change of the phase difference calculated by said phase difference change calculating means is greater that a predetermined reference value.

7. A blood pressure monitor apparatus according to claim 6, wherein one of said pair of heartbeat-synchronous wave sensors includes said cuff, a pressure sensor for detecting a pressure of the cuff, and a band-pass filter for extracting, as one of said heartbeat-synchronous waves, a cuff pulse wave produced in synchronism with the heartbeat of the living subject, from the pressure of the cuff detected by the pressure sensor.

8. A blood pressure monitor apparatus according to claim 7, further comprising a cuff-pressure increasing device which increases, at a predetermined period, said pressure of said cuff up to a predetermined pressure value, while said blood pressure measuring device does not operate, wherein said phase difference calculating means calculates a phase difference between a cuff pulse wave produced in said cuff inflated by said cuff-pressure increasing device and a pulse wave detected by the other of said pair of heartbeat-synchronous wave sensors which is adapted to be worn on a portion of the living subject different from a portion on which the cuff is adapted to be worn.

9. A blood pressure monitor apparatus according to claim 6, further comprising a cuff-pressure increasing device for increasing, at a predetermined period, said pressure of said cuff up to a predetermined pressure value, while said blood pressure measuring device does not operate, wherein said phase difference calculating means calculates a phase difference between a cuff pulse wave produced in said cuff inflated by said cuff-pressure increasing device and a pulse-synchronous wave detected by the other of said pair of pulse-synchronous wave sensors which is adapted to be worn on a portion of the living subject different from a portion on which the cuff is adapted to be worn.

10. A blood pressure monitor apparatus according to claim 6, wherein the other of said pair of heart-synchronous wave sensors includes a photoelectric pulse wave sensor which includes a light-emitting element and a light-receiving element and detects, through said light-receiving element, a photoelectric pulse wave based on a variation in quantity of light transmitted through, or reflected from, a portion of the living subject, the light being emitted from said light-emitting element toward a surface of said portion of the living subject.

11. A blood pressure monitor apparatus including a blood pressure measuring device for measuring a blood pressure value of a living subject based on variation of a pulse-synchronous wave obtained through a cuff adapted to be worn on the living subject by changing a pressure of the cuff, a pressure pulse wave sensor adapted to be pressed on an artery of the living subject for detecting a pressure pulse wave produced from the artery of the living subject, a pressure pulse wave-blood pressure relationship determining means for determining, at a predetermined period, a pressure pulse wave-blood pressure relationship between magnitude of pressure pulse wave and blood pressure, based on the pressure pulse wave detected by said pulse wave sensor and the blood pressure measured by said blood pressure measuring device, by starting said blood pressure measuring device at said predetermined period, and a monitor blood pressure determining means for successively determining a monitor blood pressure value based on an actual pressure pulse wave detected by said pressure pulse wave sensor, according to said pressure pulse wave-blood pressure relationship, the blood pressure monitor apparatus being characterized by comprising:

an electrocardiographic waveform detecting device for detecting an electrocardiographic waveform of the living subject;

a phase difference calculating means for calculating a phase difference between the pressure pulse wave detected by said pressure pulse wave sensor and the electrocardiographic waveform detected by said electrocardiographic waveform detecting device; and a starting means for starting a blood pressure measurement of said blood pressure measuring device, for updating said pressure pulse wave-blood pressure relationship, when a change of the monitor blood pressure values determined by said monitor blood pressure determining means differs from a change of respective inverses of the phase differences calculated by said phase difference calculating means.

12. A blood pressure monitor apparatus including a blood pressure measuring device for measuring a blood pressure value of a living subject based on change of a pulse wave obtained through a cuff adapted to be worn on the living subject by changing a pressure of the cuff, the blood pressure monitor apparatus comprising:

two heartbeat-synchronous wave sensors for detecting, on different portions of the living subject, respective heartbeat-synchronous waves produced in synchronism with a heartbeat of the living subject;

a phase difference calculating means for calculating a phase difference between one of the heartbeat-synchronous waves detected by one of said two heartbeat-synchronous wave sensors and the other of the heartbeat-synchronous waves detected by the other of said two heartbeat-synchronous wave sensors; and a judging means for judging whether a blood pressure measurement of said blood pressure measuring device is needed, based on the phase difference calculated by said phase difference calculating means.

13. A blood pressure monitor apparatus according to claim 12, wherein said other of said two heartbeat-synchronous wave sensors comprises a pressure pulse wave sensor adapted to be pressed on an artery of the living subject for detecting said other of the heartbeat-synchronous waves.

14. A blood pressure monitor apparatus according to claim 12, wherein said other of said two heartbeat-synchronous wave sensors comprises a photoelectric pulse wave sensor which includes a light-emitting element and a light-receiving element and detects, through said light-receiving element, a photoelectric pulse wave based on a variation in quantity of light transmitted through, or reflected from, a portion of the living subject, the light being emitted from said light-emitting element toward a surface of said portion of the living subject.

15. A blood pressure monitor apparatus according to claim 12, wherein said one of said two heartbeat-synchronous wave sensors comprises said cuff, a pressure sensor for detecting a pressure of the cuff, and a band-pass filter for extracting, as one of said heartbeat-synchronous waves, a cuff pulse wave produced in synchronism with the heartbeat of the living subject, from the pressure of the cuff detected by the pressure sensor.

16. A blood pressure monitor apparatus according to claim 15, wherein said other of said two heartbeat-synchronous wave sensors comprises a pressure pulse wave sensor adapted to be pressed on an artery of the living subject for detecting said other of the heartbeat-synchronous waves.

17. A blood pressure monitor apparatus according to claim 15, wherein said other of said two heartbeat-synchronous wave sensors comprises a photoelectric pulse wave sensor which includes a light-emitting element and a light-receiving element and detects, through said light-receiving element, a photoelectric pulse wave based on a variation in quantity of light transmitted through, or reflected from, a portion of the living subject, the light being emitted from said light-emitting element toward a surface of said portion of the living subject.

18. A blood pressure monitor apparatus according to claim 15, wherein said other of said two heartbeat-synchronous wave sensors comprises a pressure pulse wave sensor adapted to be pressed on an artery of the living subject for detecting said other of the heartbeat-synchronous waves.

19. A blood pressure monitor apparatus according to claim 12, wherein said one of said two heartbeat-synchronous wave sensors comprises an electrocardiographic waveform detecting device for detecting an electrocardiographic waveform through electrodes which are put on a surface of the living subject.

* * * * *